(12) United States Patent
Wu et al.

(10) Patent No.: US 11,322,694 B2
(45) Date of Patent: May 3, 2022

(54) ELECTROLUMINESCENT MATERIAL, METHOD FOR MANUFACTURING SAME, AND LIGHT EMITTING DEVICE

(71) Applicant: Wuhan China Star Optoelectronics Semiconductor Display Technology Co., Ltd., Wuhan (CN)

(72) Inventors: Kailong Wu, Wuhan (CN); Qu Zhang, Wuhan (CN)

(73) Assignee: Wuhan China Star Optoelectronics Semiconductor Display Technology Co., Ltd., Wuhan (CN)

(*) Notice: Subject to any disclaimer, the term of this patent is extended or adjusted under 35 U.S.C. 154(b) by 323 days.

(21) Appl. No.: 16/611,486

(22) PCT Filed: Sep. 18, 2019

(86) PCT No.: PCT/CN2019/106408
§ 371 (c)(1),
(2) Date: Nov. 7, 2019

(87) PCT Pub. No.: WO2020/192042
PCT Pub. Date: Oct. 1, 2020

(65) Prior Publication Data
US 2021/0336152 A1 Oct. 28, 2021

(30) Foreign Application Priority Data

Mar. 27, 2019 (CN) .......................... 201910239980.3

(51) Int. Cl.
*C07D 219/14* (2006.01)
*H01L 51/00* (2006.01)
*C07D 401/14* (2006.01)
*C09K 11/06* (2006.01)
*H01L 51/50* (2006.01)

(52) U.S. Cl.
CPC ........ *H01L 51/0072* (2013.01); *C07D 219/14* (2013.01); *C07D 401/14* (2013.01); *C09K 11/06* (2013.01); *H01L 51/0058* (2013.01); *H01L 51/0067* (2013.01); *C09K 2211/1007* (2013.01); *C09K 2211/1011* (2013.01);
(Continued)

(58) Field of Classification Search
None
See application file for complete search history.

(56) References Cited

FOREIGN PATENT DOCUMENTS

| CN | 105503766 | 4/2016 |
|---|---|---|
| CN | 107046100 | 8/2017 |

(Continued)

*Primary Examiner* — Clinton A Brooks

(57) ABSTRACT

The present application provides an electroluminescent material, a method for manufacturing an electroluminescent material, and a light emitting device, by employing the strong electron-withdrawing group such as cyano, pyridine, pyrimidine, or s-triazine to enhance the electron-withdrawing property of the fluorenone receptor unit, a captodative electron effect between the electron donor unit and the electron acceptor unit in the molecule is enhanced, so that the intermolecular charge transfer property is enhanced while the red light shifts, thereby further reducing the energy level difference between the single-line energy level and the triplet energy level of the target molecule, to realize a long life span, red light emitted electroluminescent material, a method for manufacturing the electroluminescent material and a light emitting device.

20 Claims, 1 Drawing Sheet

(52) U.S. Cl.
CPC .. *C09K 2211/1018* (2013.01); *H01L 51/5012* (2013.01); *H01L 51/5056* (2013.01); *H01L 51/5072* (2013.01)

(56) References Cited

FOREIGN PATENT DOCUMENTS

| | | |
|---|---|---|
| CN | 107056701 | 8/2017 |
| CN | 108264479 | 7/2018 |

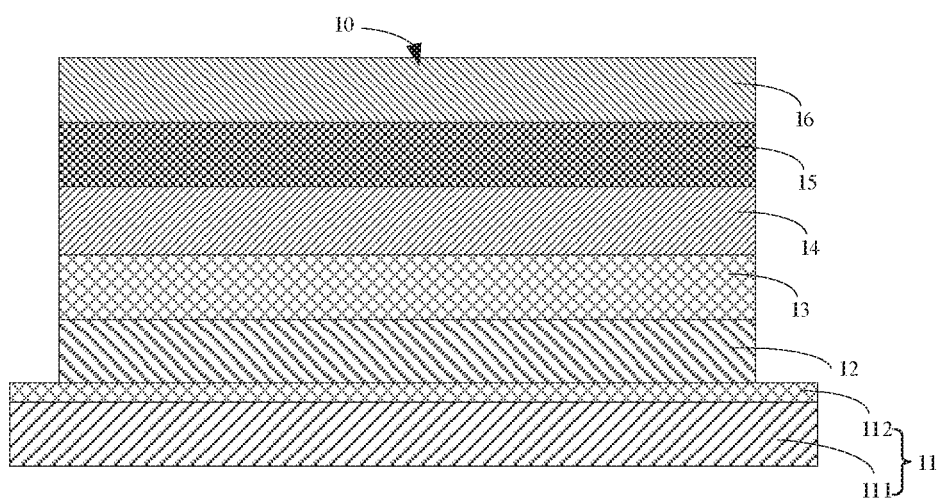

ELECTROLUMINESCENT MATERIAL, METHOD FOR MANUFACTURING SAME, AND LIGHT EMITTING DEVICE

RELATED APPLICATIONS

This application is a National Phase of PCT Patent Application No. PCT/CN2019/106408 having International filing date of Sep. 18, 2019, which claims the benefit of priority of Chinese Patent Application No. 201910239980.3 filed on Mar. 27, 2019. The contents of the above applications are all incorporated by reference as if fully set forth herein in their entirety.

FIELD AND BACKGROUND OF THE INVENTION

The present application relates to a display field, and particularly to an electroluminescent material, a method for manufacturing the electroluminescent material, and a light emitting device.

In prior art, organic light emitting diodes (OLEDs) are self-luminous, where electroluminescent material is a material that mainly dominates emitted light; however, luminous efficiency of the existing electroluminescent material is poor, which often leads to failure of an organic light emitting diode, therefore, it is necessary to provide an electroluminescent material, a method for manufacturing the electroluminescent material, and a light emitting device with a long life span and red-emitting.

SUMMARY OF THE INVENTION

The present application provides an electroluminescent material, a method for manufacturing the electroluminescent material, and a light emitting device, to realize an electroluminescent material, a method for manufacturing the electroluminescent material, and a light emitting device with a long life span and red light emitted.

The present application provides an electroluminescent material, wherein a structural formula of the electroluminescent material is

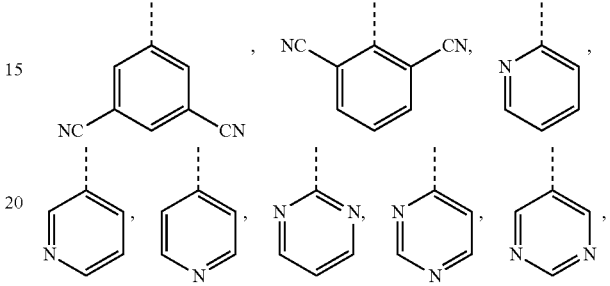

wherein a structural formula of $R_1$ group comprises one of

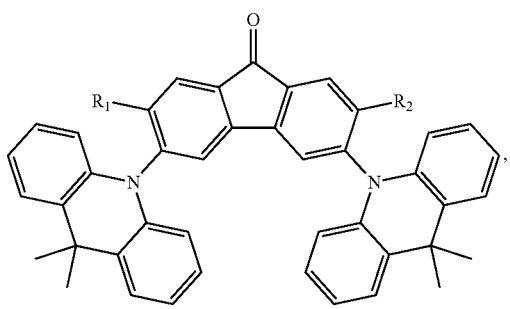

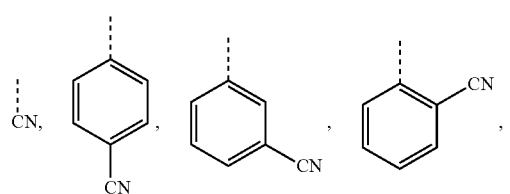

-continued

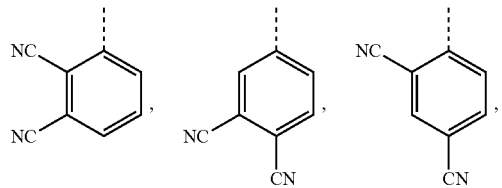

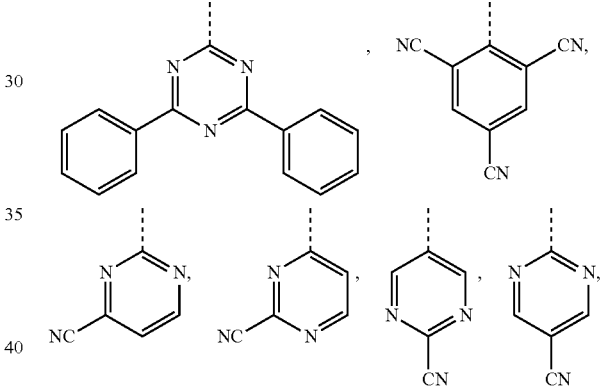

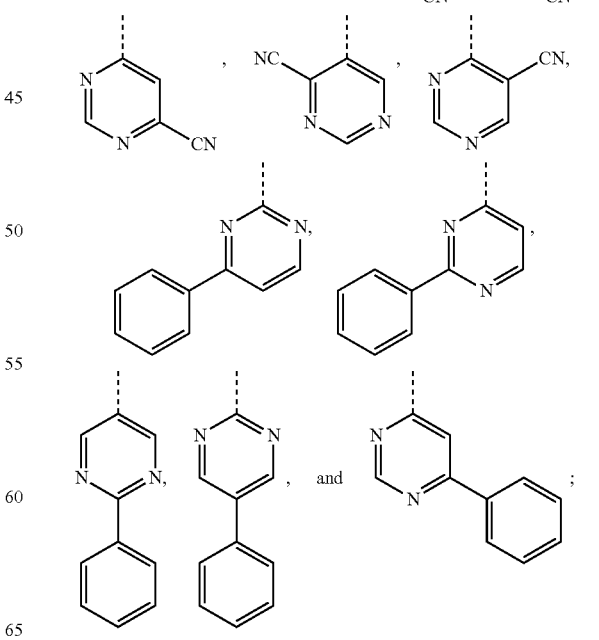

and a structural formula of R2 group comprises one of

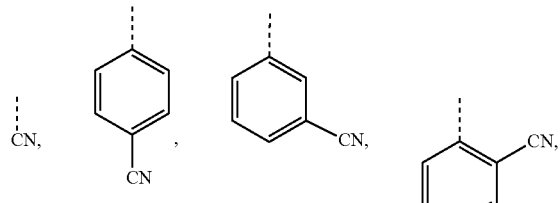

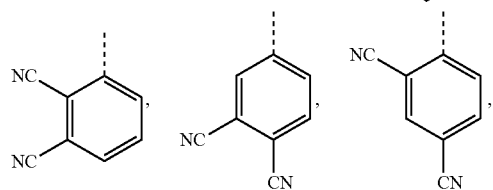

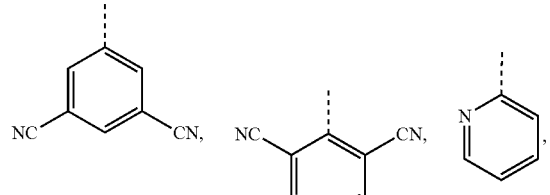

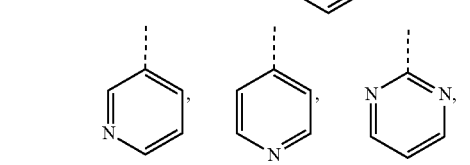

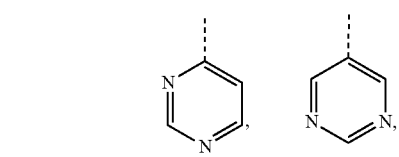

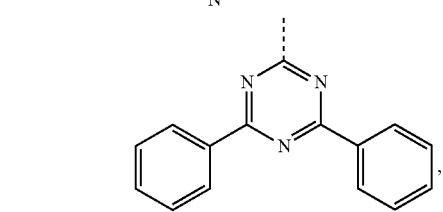

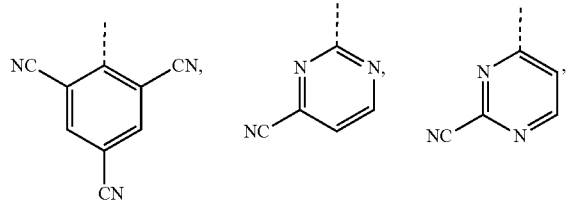

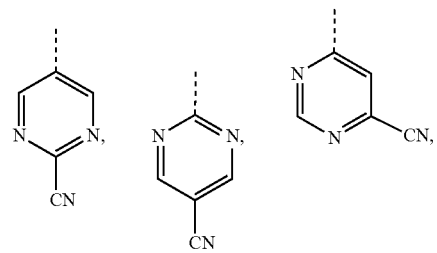

-continued

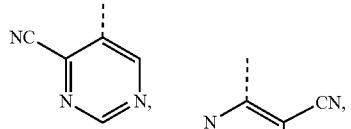

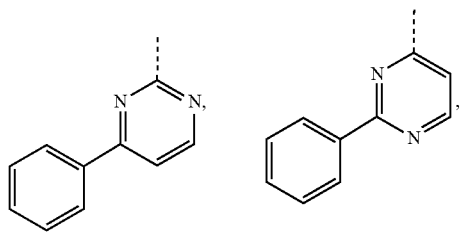

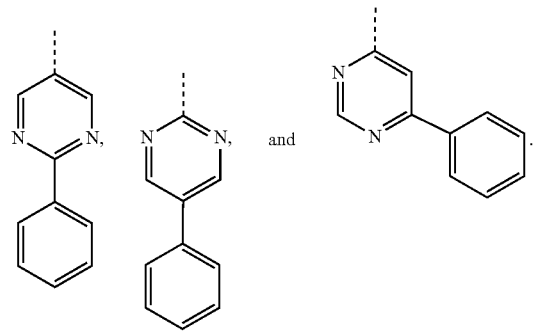

and

A method for manufacturing the electroluminescent material, including:

providing a first reactant and a second reactant, and reacting the first reactant and the second reactant to generate a first intermediate product, wherein a structural formula of the first reactant is

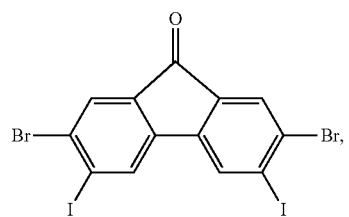 [SMILES: O=C1c2cc(Br)c(I)cc2-c2cc(I)c(Br)cc21]

a structural formula of the second reactant is

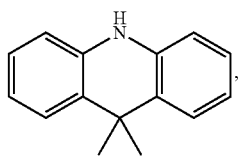 [SMILES: CC1(C)c2ccccc2Nc2ccccc21]

and a structural formula of the first intermediate product is

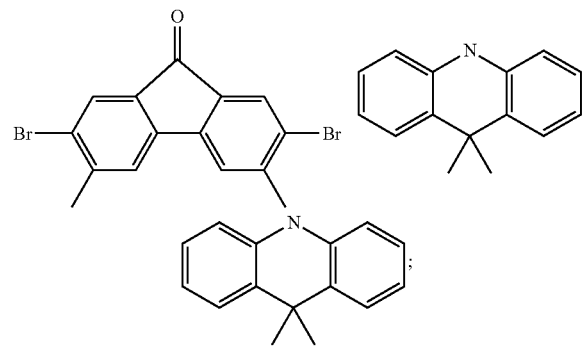

and
providing a third reactant, and reacting the first intermediate product and the third reactant to generate the electroluminescent material, wherein the third reactant comprises a compound containing $R_1$ group and a compound containing $R_2$ group, and a structural formula of the electroluminescent material is

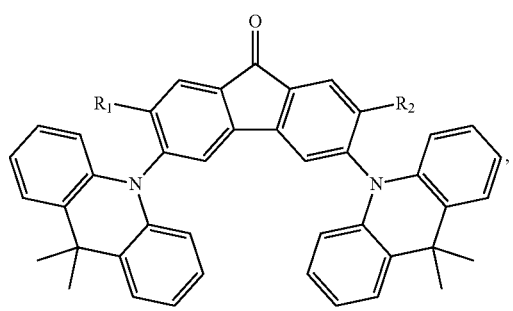

wherein a structural formula of $R_1$ group comprises one of

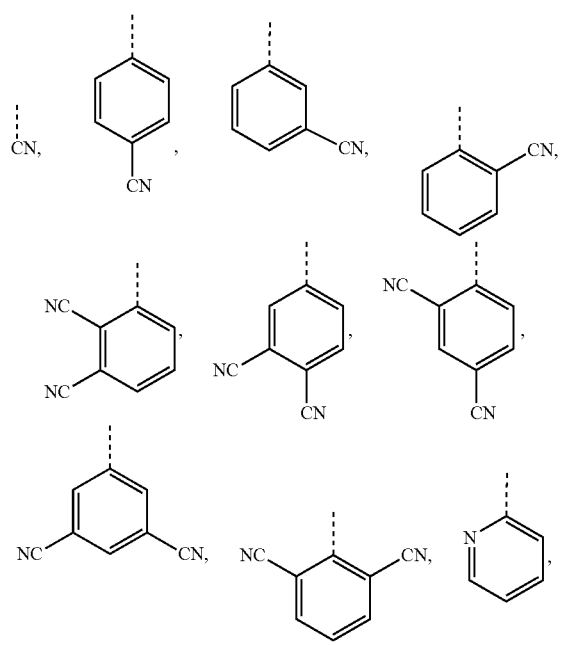

-continued

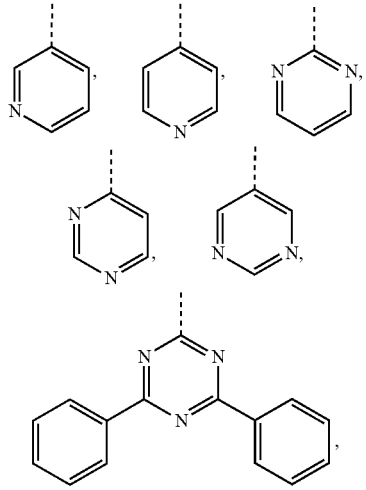

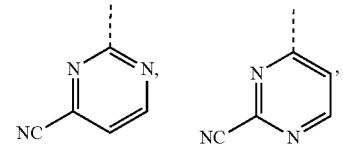

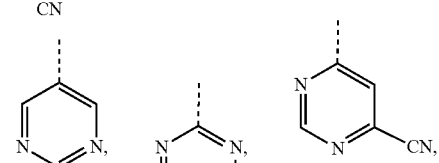

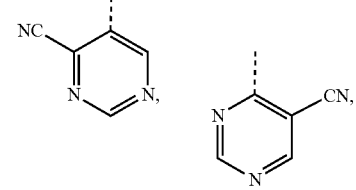

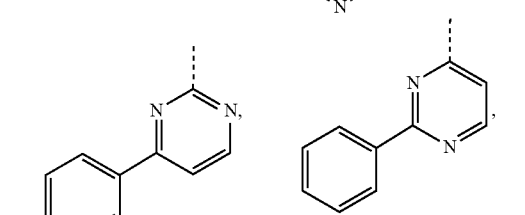

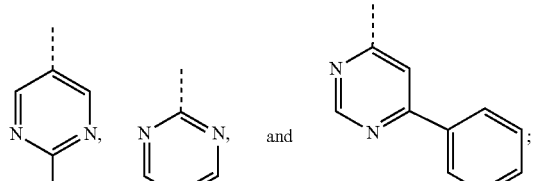 and 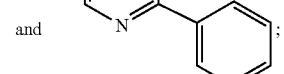

and a structural formula of R$_2$ group comprises one of

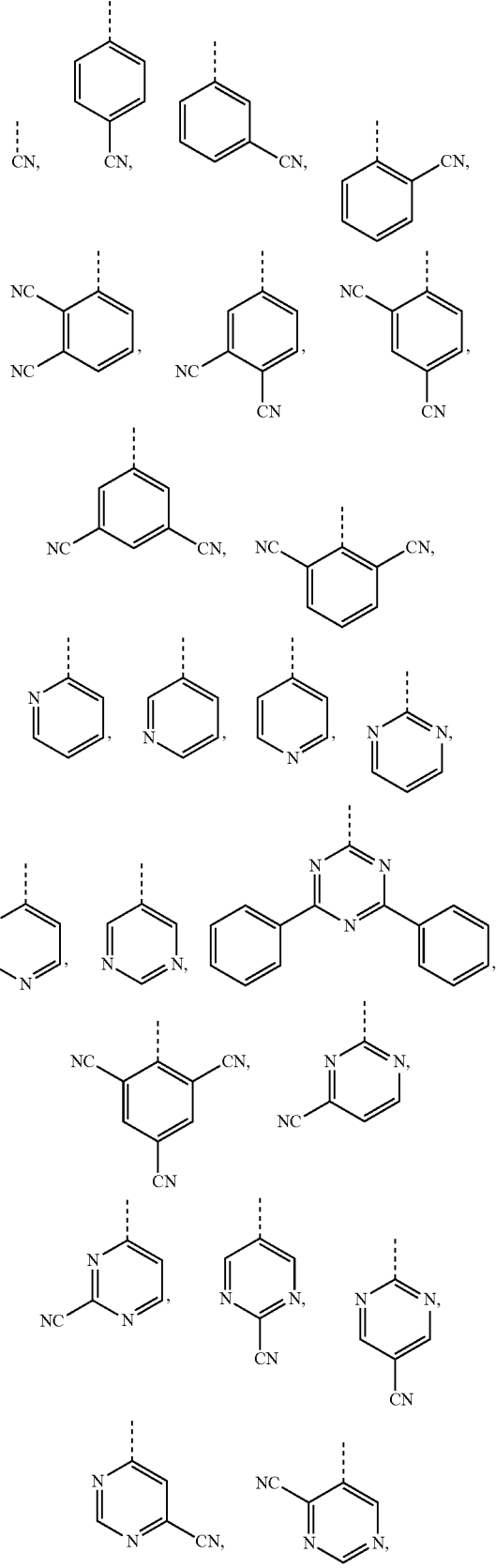

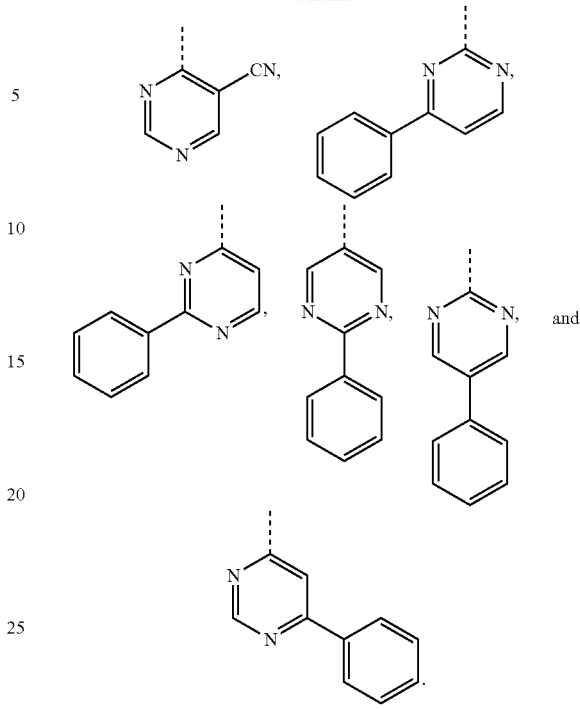

In the method for manufacturing the electroluminescent material of the present application, in the step of reacting the first reactant and the second reactant to generate a first intermediate product, a relationship between a molar quantity of the first reactant and a molar quantity of the second reactant is that for 10 millimoles of the first reactant, there are 15 millimoles-25 millimoles of the second reactant.

In the method for manufacturing an electroluminescent material of the present application, the first reactant and the second reactant are reacted in a first solvent to generate the first intermediate product, and the first solvent comprises toluene, ethanol, ethylene, perchloroethylene, trichloroethylene, acetone, ethylene glycol ether, triethanolamine, or combinations thereof.

In the method for manufacturing an electroluminescent material of the present application, wherein the first solvent comprises a first additive, the first additive comprises tris(dibenzylideneacetone)dipalladium, tetrakistriphenylphosphine palladium, 9,10-dihydro-9,9-diphenyl acridine, bis(2-diphenylphosphinophenyl)ether, cesium carbonate, potassium hydroxide, sodium hydroxide, sodium tert-butoxide, sodium bicarbonate, or combinations thereof.

In the method for manufacturing an electroluminescent material of the present application, in the step of providing a third reactant, and reacting the first intermediate product and the third reactant to generate the electroluminescent material, the R$_1$ group and the R$_2$ group are the same, a relationship between a molar quantity of the first intermediate product and a molar quantity of the third reactant is that for 5 millimoles of the first intermediate product, there are 10 millimoles-40 millimoles of the third reactant.

In the method for manufacturing an electroluminescent material of the present application, the first intermediate product and the third reactant are reacted in a second solvent to generate the electroluminescent material, and the second solvent comprises water, N-methylpyrrolidone, toluene, ethanol, ethylene, perchloroethylene, trichloroethylene, acetone, ethylene glycol ether, triethanolamine, or combinations thereof.

In the method for manufacturing an electroluminescent material of the present application, the second solvent comprises a second additive, and the second additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In the method for manufacturing an electroluminescent material of the present application, in the step of providing a third reactant, and reacting the first intermediate product and the third reactant to generate the electroluminescent material, the $R_1$ group and the $R_2$ group are different, and the third reactant comprises a first sub-reactant and a second sub-reactant, wherein the step of providing a third reactant, and reacting the first intermediate product and the third reactant to generate the electroluminescent material comprises:

providing the first sub-reactant, and reacting the first intermediate product and the first sub-reactant to generate the second intermediate product, the first sub-reactant comprises a compound containing the $R_1$ group, and a structural formula of the second intermediate product comprises

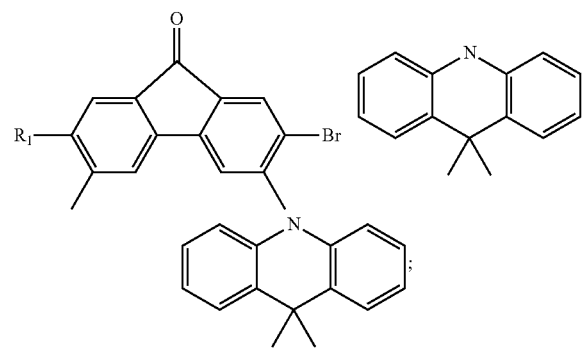

and providing the second sub-reactant, and reacting the second intermediate product and the second sub-reactant to generate the electroluminescent material, wherein the second reactant comprises a compound containing the $R_2$ group.

In the method for manufacturing an electroluminescent material of the present application, in the step of providing a first sub-reactant, and reacting the first intermediate product and the first sub-reactant to generate the second intermediate product, a relationship between a molar quantity of the first intermediate product and a molar quantity of the first sub-reactant is that for 5 millimoles of the first intermediate product, there are 3 millimoles-8 millimoles of the first sub-reactant.

In the method for manufacturing an electroluminescent material of the present application, the first intermediate product and the first sub-reactant are reacted in a third solvent to generate the second intermediate product, the third solvent comprises water, N-methylpyrrolidone, toluene, ethanol, ethylene, perchloroethylene, trichloroethylene, acetone, ethylene glycol ether, triethanolamine, or combinations thereof.

In the method for manufacturing an electroluminescent material of the present application, the third solvent comprises a third additive, and the third additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In the method for manufacturing an electroluminescent material of the present application, in the step of providing a second sub-reactant, and reacting the second intermediate product and the second sub-reactant to generate the electroluminescent material, a relationship between a molar quantity of the second intermediate product and a molar quantity of the second sub-reactant is that for 4 millimoles of the second intermediate product, there are 3 millimoles-8 millimoles of the second sub-reactant.

In the method for manufacturing an electroluminescent material of the present application, the second intermediate product and the second sub-reactant are reacted in a fourth solvent to generate to the electroluminescent material, the fourth solvent comprises water, N-methylpyrrolidone, toluene, ethanol, ethylene, perchloroethylene, trichloroethylene, acetone, ethylene glycol ether, triethanolamine, or combinations thereof.

In the method for manufacturing an electroluminescent material of the present application, the fourth solvent comprises a fourth additive, the fourth additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In the method for manufacturing an electroluminescent material of the present application, the step of providing a third reactant, and reacting the first intermediate product and the third reactant to generate the electroluminescent material comprises:

providing a third reactant, and reacting the first intermediate product and the third reactant to generate a mixture containing the electroluminescent material; and separating and purifying the mixture containing the electroluminescent material to obtain the electroluminescent material.

In the method for manufacturing an electroluminescent material of the present application, in the step of separating and purifying the mixture containing the electroluminescent material to obtain the electroluminescent material, an extraction solvent is employed to extract the mixture, and a chromatographic column is employed for chromatography.

In the method for manufacturing an electroluminescent material of the present application, the extraction solvent comprises dichloromethane, chloroform, tetrahydrofuran, or combinations thereof.

In the method for manufacturing an electroluminescent material of the present application, in the chromatographic column, the dichloromethane and the n-hexane have a volume ration ranging from 1:0.5 to 1:10.

A light emitting device includes:

a substrate layer, wherein the substrate layer comprises a base and a first electrode layer formed on the base;

a hole transport layer, wherein the hole transport layer is formed on the substrate layer, and is electrically connected to the first electrode layer;

an auxiliary layer, wherein the auxiliary layer is formed on the hole transport layer;

a light emitting layer, wherein the light emitting layer is formed on the auxiliary layer;

an electron transport layer, wherein the electron transport layer is formed on the light emitting layer; and a second electrode layer, wherein the second electrode is electrically connected to the electron transport layer, wherein the light emitting layer comprises the electroluminescent material, and a structural formula of the electroluminescent material is

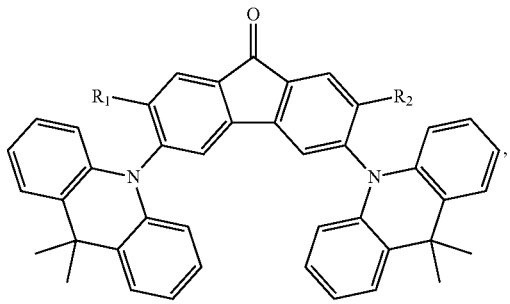

wherein a structural formula of R₁ group comprises one of

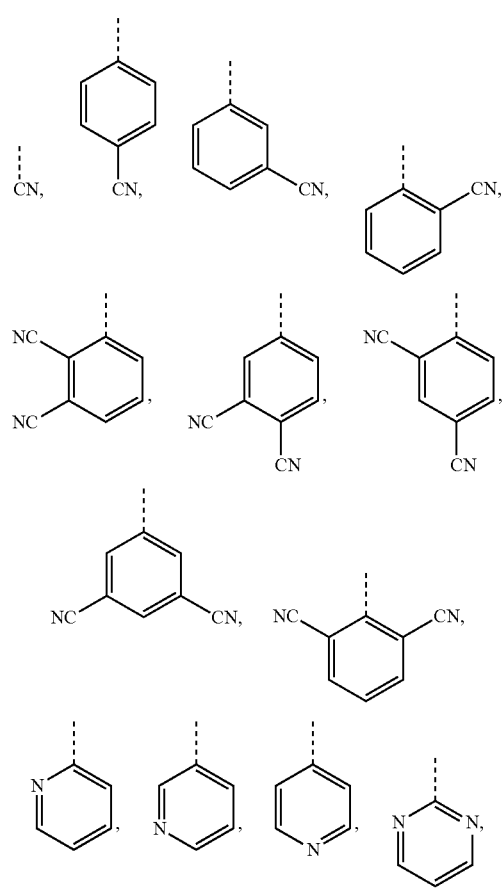

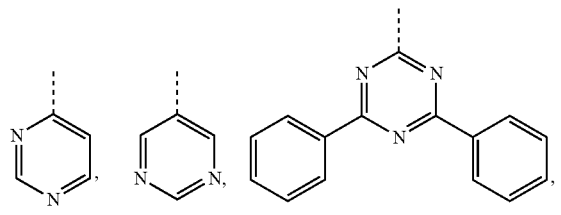

-continued

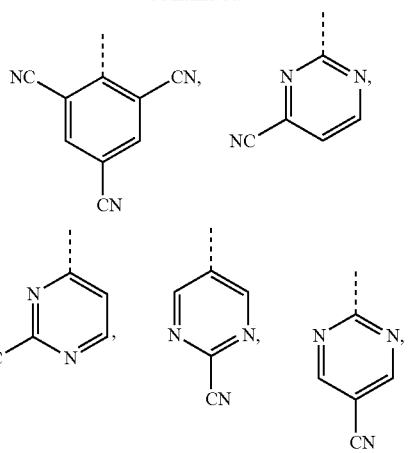

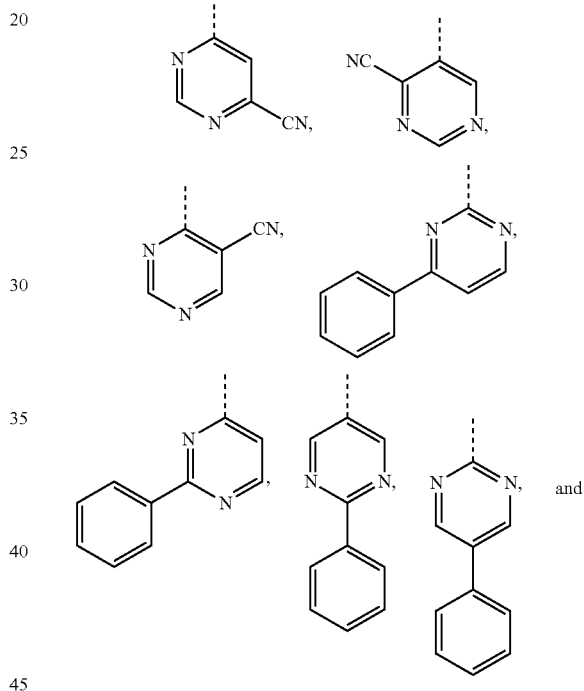

and a structural formula of R₂ group comprises one of

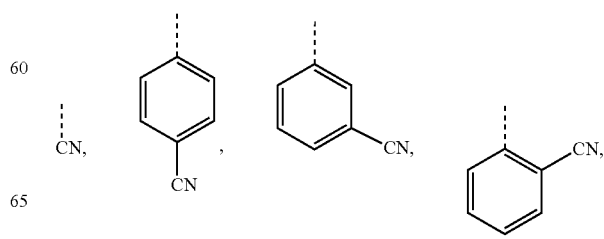

-continued
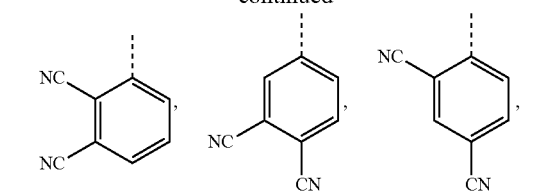
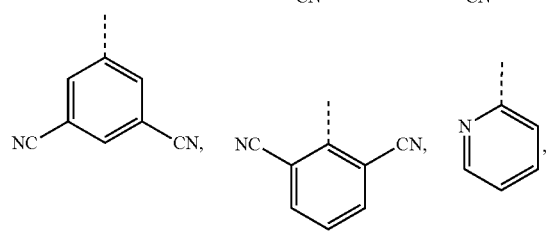
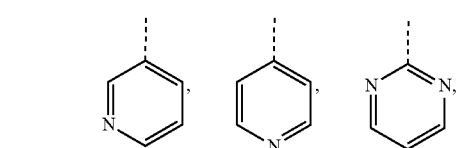
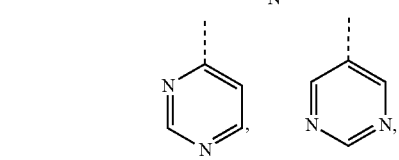
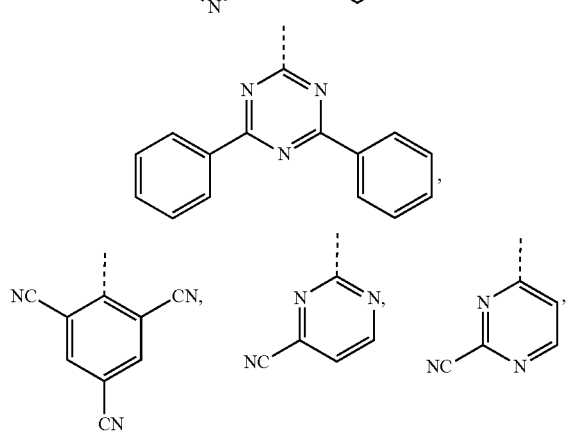
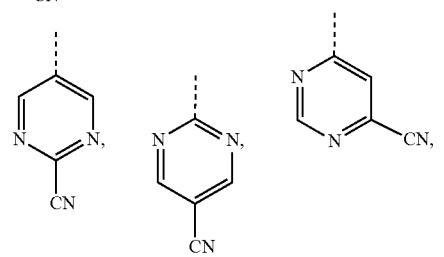
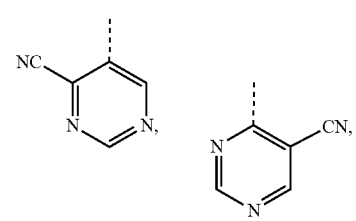
-continued
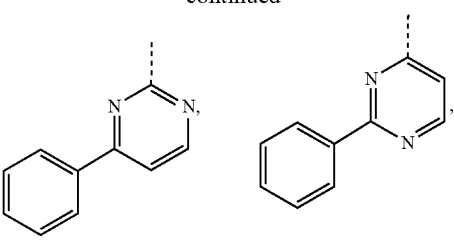
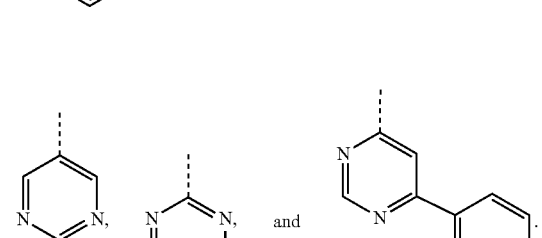 and 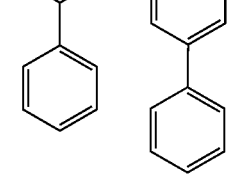
The benefit is: the present application provides an electroluminescent material, a method for manufacturing the electroluminescent material, and a light emitting device, and a structural formula of the electroluminescent material is
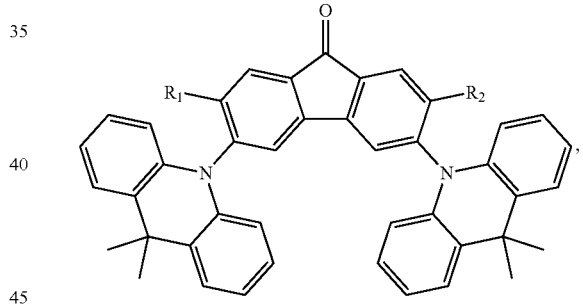
wherein structural formulas of the $R_1$ and $R_2$ are selected from
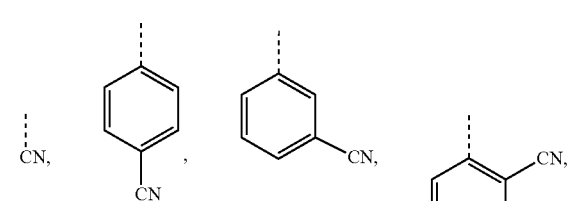
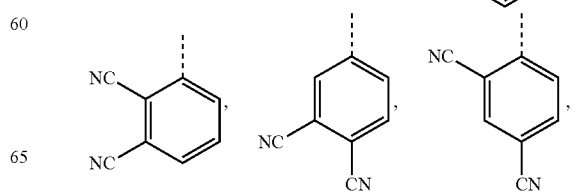

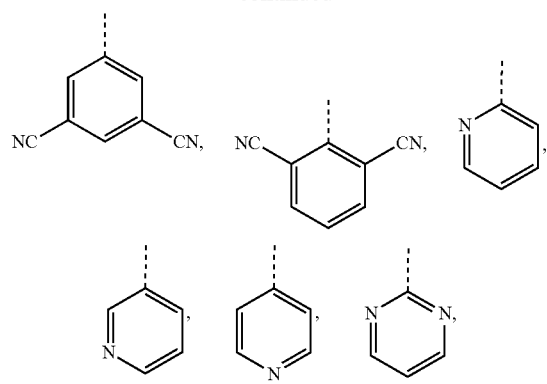
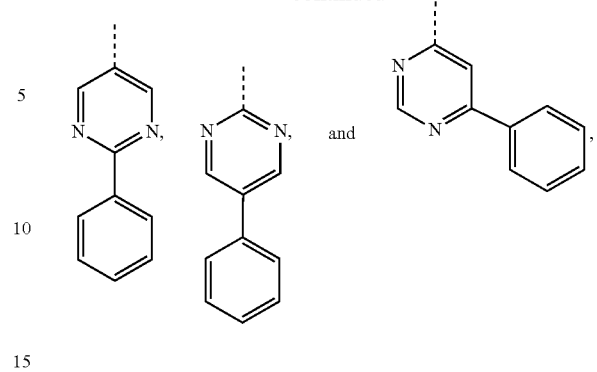
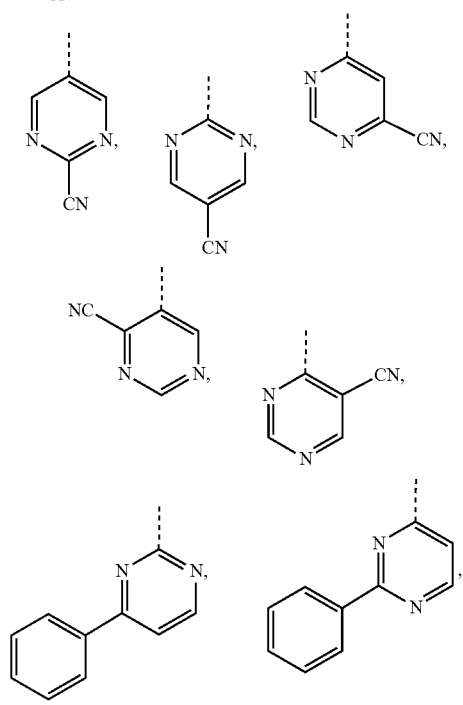

by employing the strong electron-withdrawing group such as cyano, pyridine, pyrimidine, or s-triazine to enhance the electron-withdrawing property of the fluorenone receptor unit, a captodative electron effect between the electron donor unit and the electron acceptor unit in the molecule is enhanced, so that the intermolecular charge transfer property is enhanced while the red light shifts, thereby further reducing the energy level difference between the single-line energy level and the triplet energy level of the target molecule, to realize a long life span, red light emitted electroluminescent material, a method for manufacturing the electroluminescent material and a light emitting device.

BRIEF DESCRIPTION OF THE SEVERAL VIEWS OF THE DRAWINGS

FIG. 1 is a schematic structural view of a light emitting device of the present application.

DESCRIPTION OF SPECIFIC EMBODIMENTS OF THE INVENTION

The present application provides an electroluminescent material. A structural formula of the electroluminescent material is

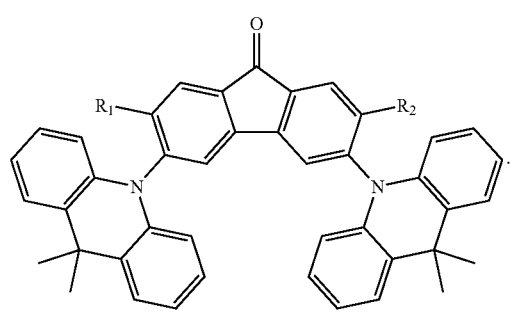

A structural formula of $R_1$ group comprises one of

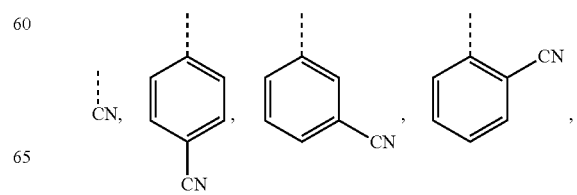

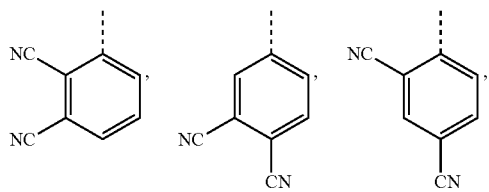
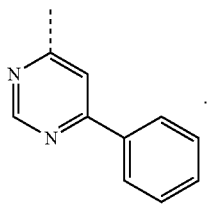
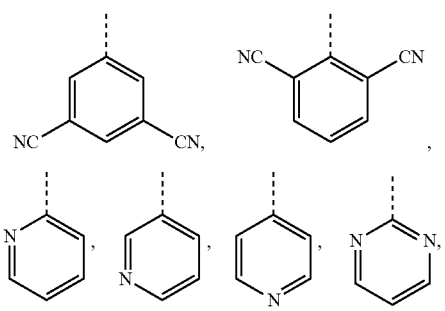
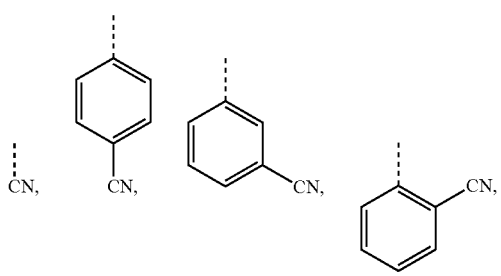
A structural formula of $R_2$ group comprises one of
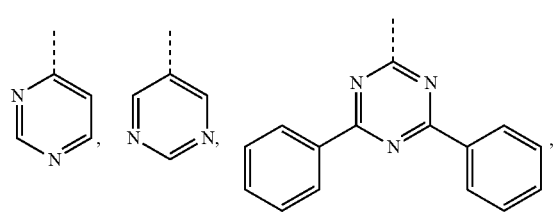
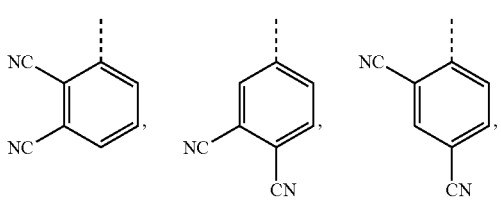
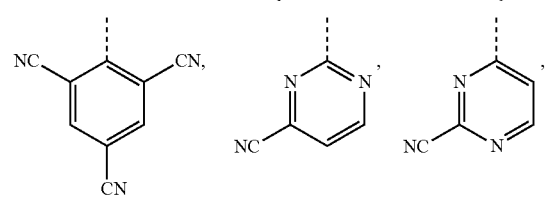
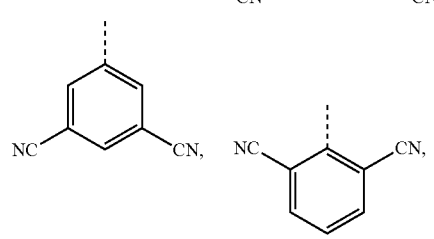
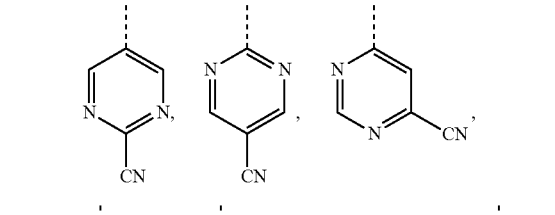
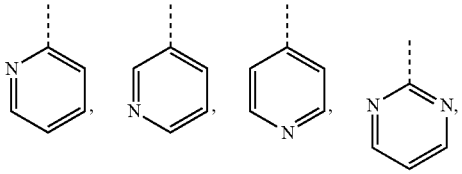
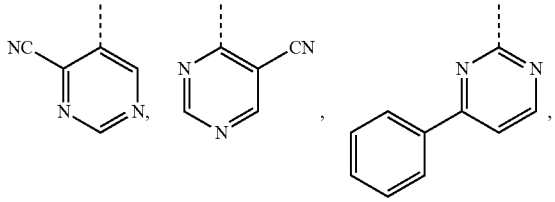
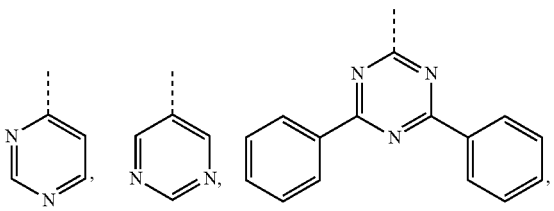, and
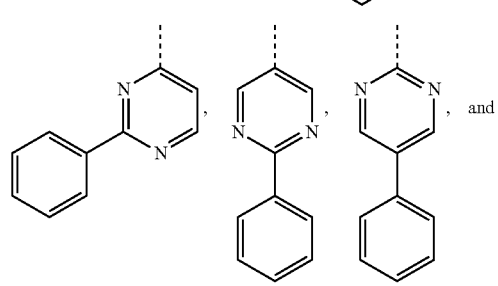
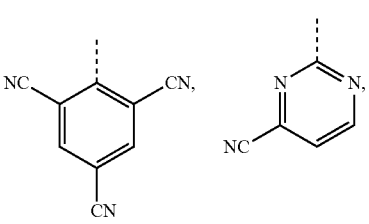

-continued

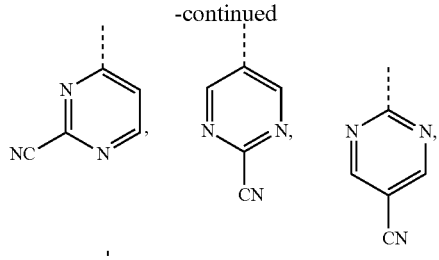

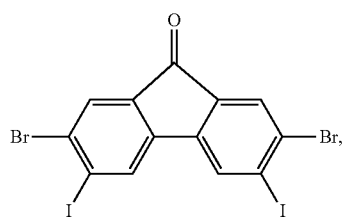

In some embodiments, the $R_1$ group and the $R_2$ group can be the same. In other embodiments, the $R_1$ group and the $R_2$ can be different.

The present application also provides a method for manufacturing the electroluminescent material. The method for manufacturing the electroluminescent material includes:

A, providing a first reactant and a second reactant, and reacting the first reactant and the second reactant to generate a first intermediate product, wherein a structural formula of the first reactant is

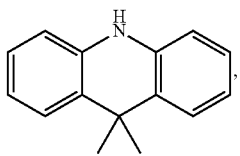 [SMILES: CC1(C)c2ccccc2Nc2ccccc21]

a structural formula of the second reactant is

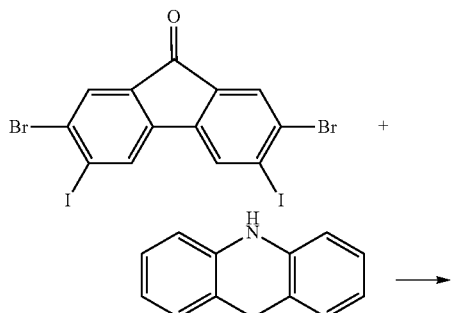

and a structural formula of the first intermediate product is

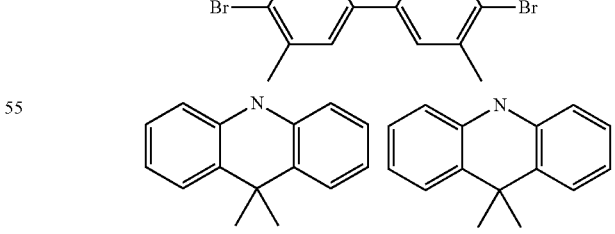

A reaction equation of reacting the first reactant and the second reactant to generate the first intermediate product can be:

In the step of reacting the first reactant and the second reactant to generate a first intermediate product, a relationship between a molar quantity of the first reactant and a molar quantity of the second reactant can be 10 millimoles of the first reactant corresponding to 15 millimoles-25 millimoles of the second reactant.

The first reactant and the second reactant are reacted in a first solvent to generate the first intermediate product, and the first solvent comprises toluene, ethanol, ethylene, perchloroethylene, trichloroethylene, acetone, ethylene glycol ether, triethanolamine, or combinations thereof. The first solvent includes a first additive, and the first additive comprises tris(dibenzylideneacetone)dipalladium, tetrakistriphenylphosphine palladium, 9,10-dihydro-9,9-diphenyl acridine, bis(2-diphenylphosphinophenyl)ether, cesium carbonate, potassium hydroxide, sodium hydroxide, sodium tert-butoxide, sodium bicarbonate, or combinations thereof.

In one embodiment, the first reactant

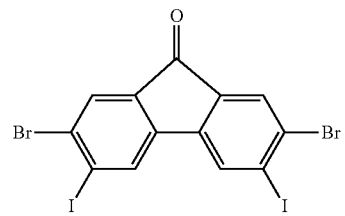 [SMILES: O=C1c2cc(Br)c(I)cc2-c2cc(I)c(Br)cc21]

and the second reactant

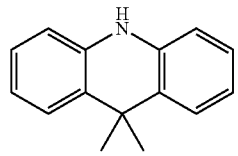 [SMILES: CC1(C)c2ccccc2Nc2ccccc21]

are added into a single-mouth bottle, and 9,10-dihydro-9,9-diphenyl acridine, tris(dibenzylideneacetone)dipalladium, bis(2-diphenylphosphinophenyl)ether, and sodium tert-butoxide are added, a relationship between a molar quantity of the first reactant and a molar quantity of the second reactant can be that for 10 millimoles of the first reactant, there are 21 millimoles of the second reactant, in an argon atmosphere, toluene is added, those are reacted 24 hours at 80 degrees Celsius to obtain a mixture containing the first intermediate product, and then a separating and purifying is employed to obtain the intermediate product

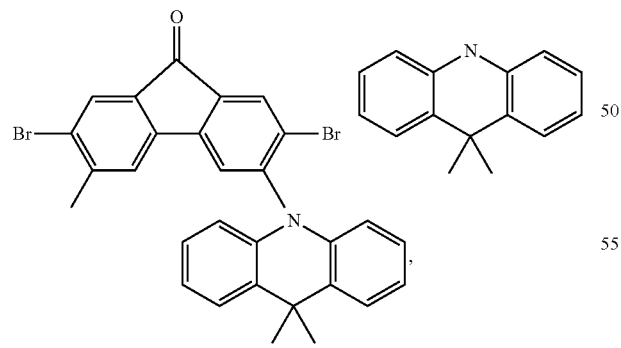

the first intermediate product is red powder.

B, providing a third reactant, and reacting the first intermediate product and the third reactant to generate the electroluminescent material, wherein the third reactant comprises a compound containing $R_1$ group and a compound containing $R_2$ group, and a structural formula of the electroluminescent material is

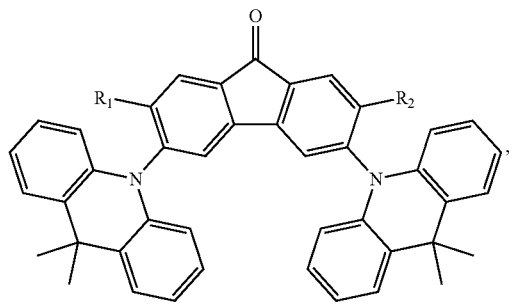

wherein a structural formula of $R_1$ group comprises one of

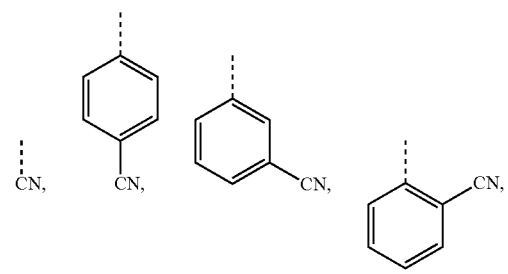

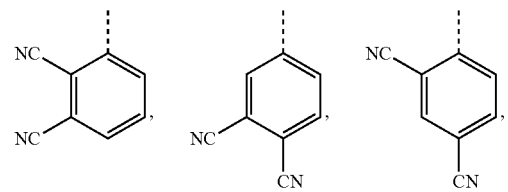

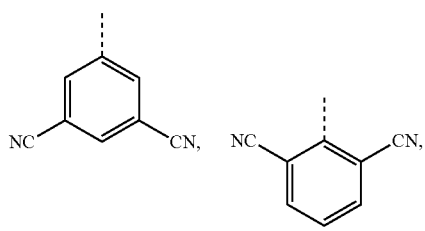

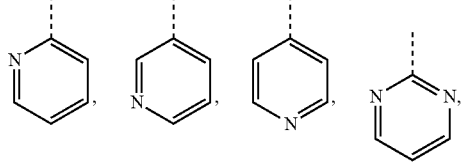

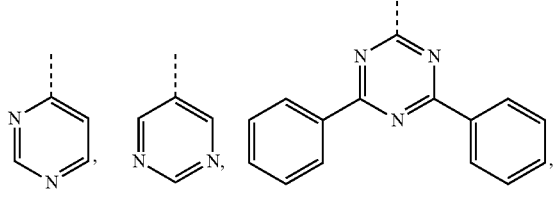

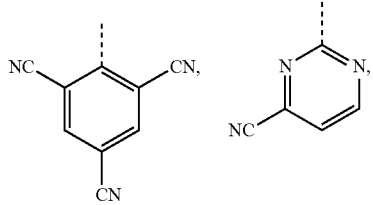

-continued

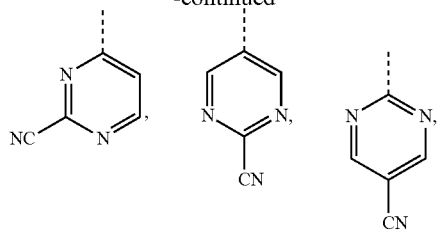

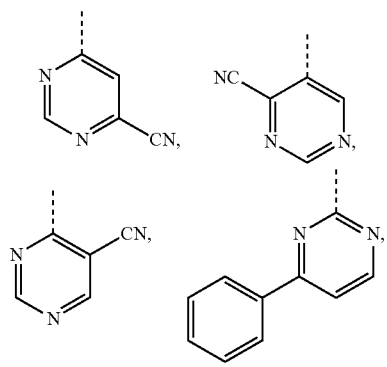

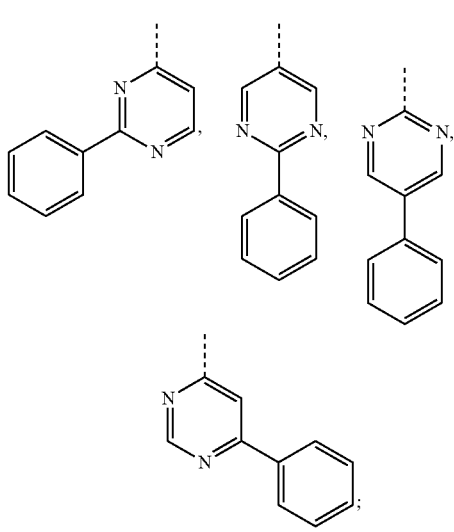

and a structural formula of R₂ group comprises one of

-continued

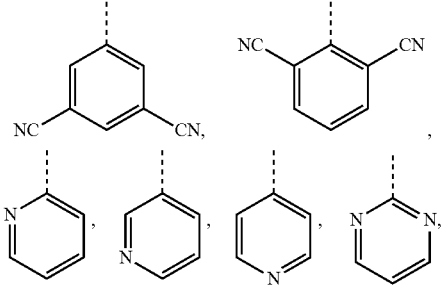

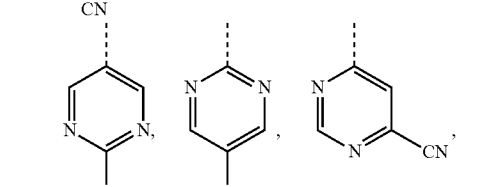

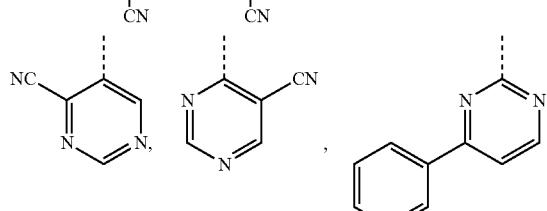

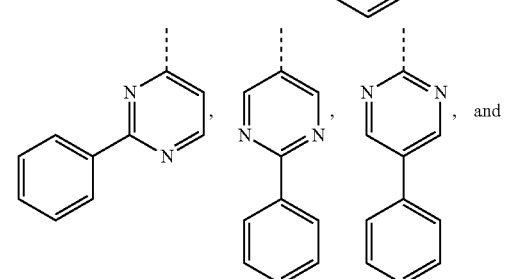

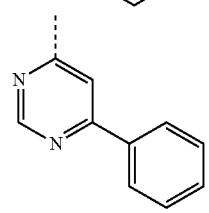

In some embodiments, the R₁ group and the R₂ group can be the same. A relationship of between a molar quantity of the first intermediate product and a molar quantity of the third reactant is that for 5 millimoles of the first intermediate product, there are 10 millimoles-40 millimoles of the third reactant.

The first intermediate product and the third reactant are reacted in a second solvent to generate the electroluminescent material. The second solvent includes water, N-methylpyrrolidone, toluene, ethanol, ethylene, perchloroethylene, trichloroethylene, acetone, ethylene glycol ether, triethanolamine, or combinations thereof. The second solvent includes a second additive, the second additive includes ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In one embodiment, the first intermediate product

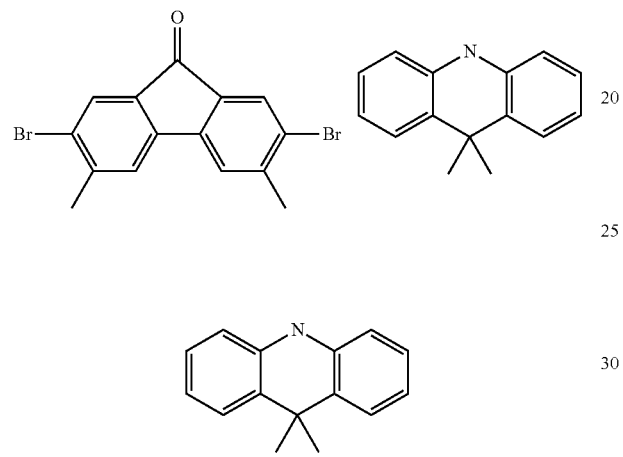

and the third reactant cuprous cyanide (CuCN) are added into a single-mouth bottle, a relationship between a molar quantity of the intermediate product and a molar quantity of the third reactant is that for 5 millimoles of the first intermediate product, there are 30 millimoles of the third reactant, and then N-methylpyrrolidone is added, those are reacted for 18 hours at 150 degrees Celsius to obtain a mixture containing the electroluminescent material, and a separating and purifying process is employed to obtain the electroluminescent material

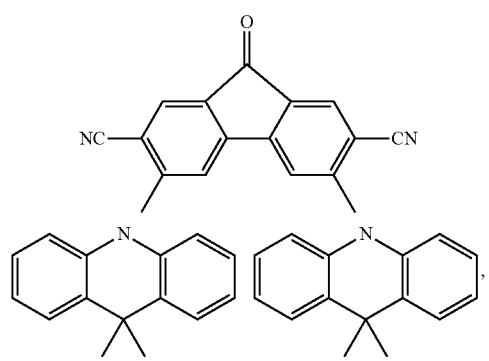

the electroluminescent material is red powder.

In one embodiment of the present application, a reaction equation of reacting the intermediate product and the third reactant is:

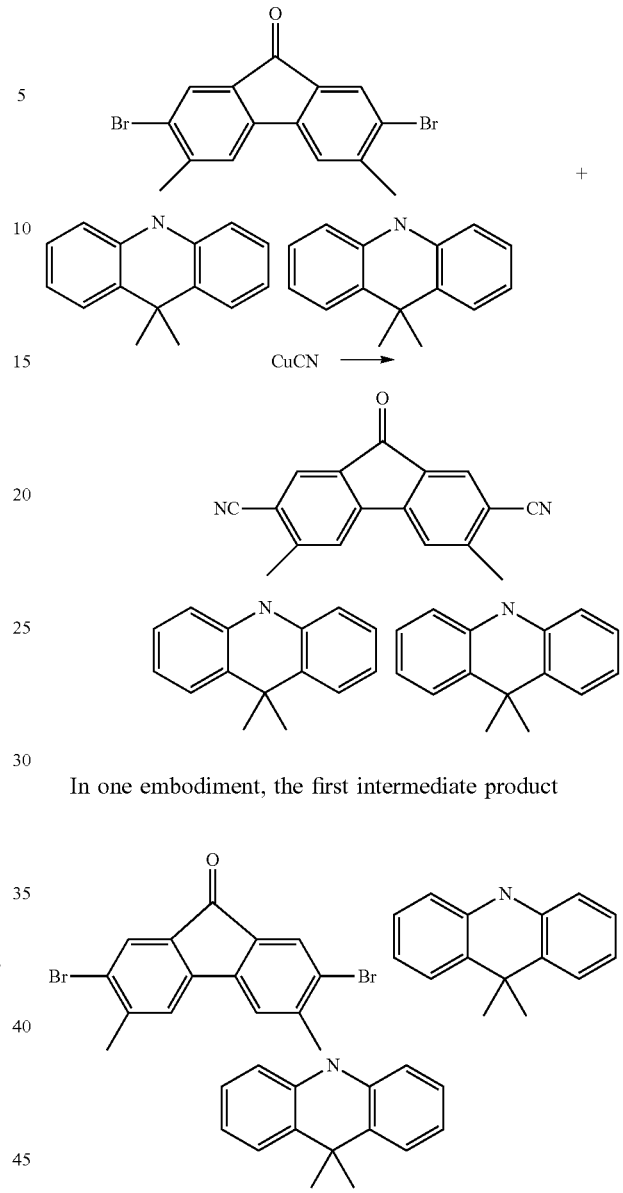

In one embodiment, the first intermediate product and the third reactant

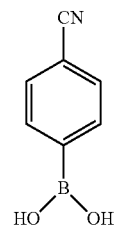

are added into a single mouth bottle, a relationship between a molar quantity of the intermediate product and a molar quantity of the third reactant is that for 5 millimoles of the first intermediate product, there are 12 millimoles of the third reactant, and then tetrakistriphenylphosphine palladium and anhydrous sodium carbonate are added, then toluene, ethanol and deionized water are added, those are reacted for 48 hours at 100 degrees Celsius to obtain a mixture containing the electroluminescent material, and then a separating and purifying process is employed to obtain the electroluminescent material

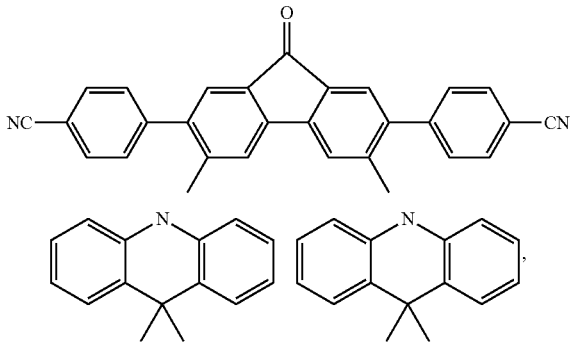

the electroluminescent material is red powder.

In this embodiment, a reaction equation of reacting the first intermediate product and the third reactant is:

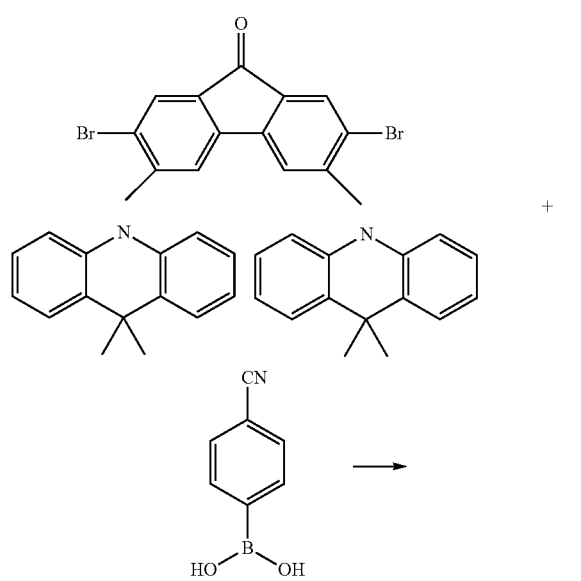

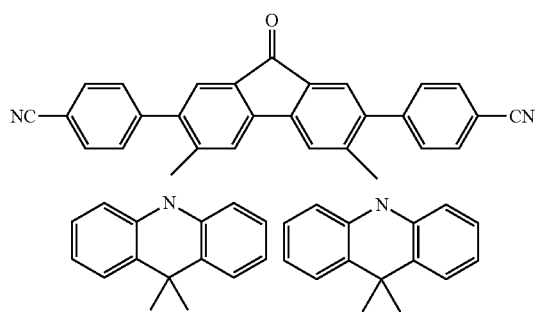

In one embodiment, the first intermediate product

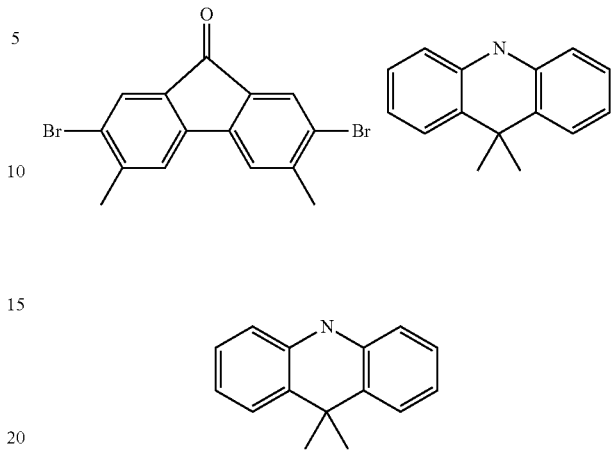

and the third reactant

are added into a single mouth bottle, a relationship between a molar quantity of the intermediate product and a molar quantity of the third reactant is that for 5 millimoles of the first intermediate product, those are 12 millimoles of the third reactant, and then tetrakistriphenylphosphine palladium and anhydrous sodium carbonate are added, then toluene, ethanol and deionized water are added, those are reacted for 48 hours at 100 degrees Celsius to obtain a mixture containing the electroluminescent material and then a separating and purifying process is employed to obtain the electroluminescent material

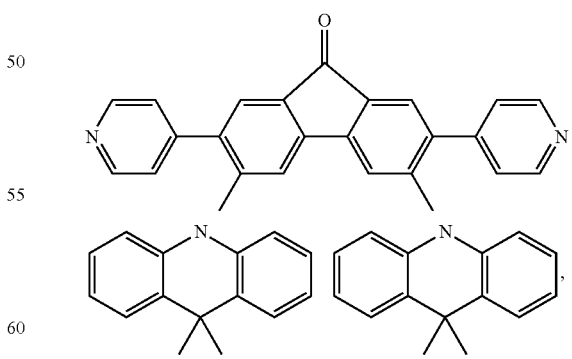

the electroluminescent material is red powder.

In one embodiment of the present application, a reaction equation of the reacting the first intermediate product and the third reactant is:

third reactant, and then tetrakistriphenylphosphine palladium and anhydrous sodium carbonate are added, then toluene, ethanol and deionized water are added, those are reacted for 48 hours at 100 degrees Celsius to obtain a mixture containing the electroluminescent material and then a separating and purifying process is employed to obtain the electroluminescent material

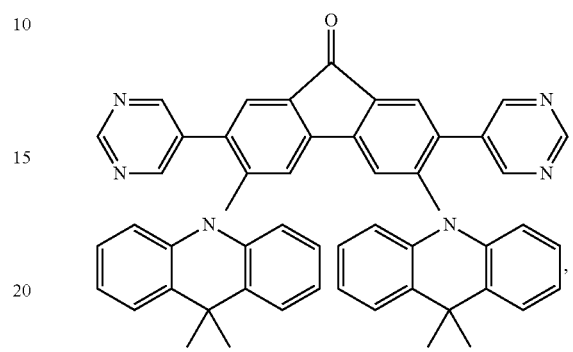

the electroluminescent material is red powder.

In one embodiment of the present application, a reaction equation of the reacting the first intermediate product and the third reactant is:

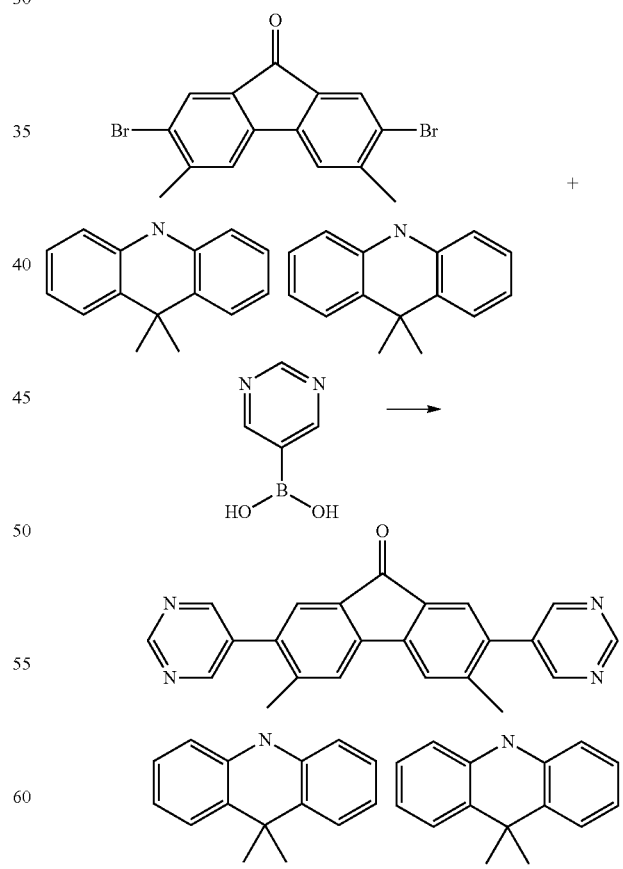

In one embodiment, the first intermediate product

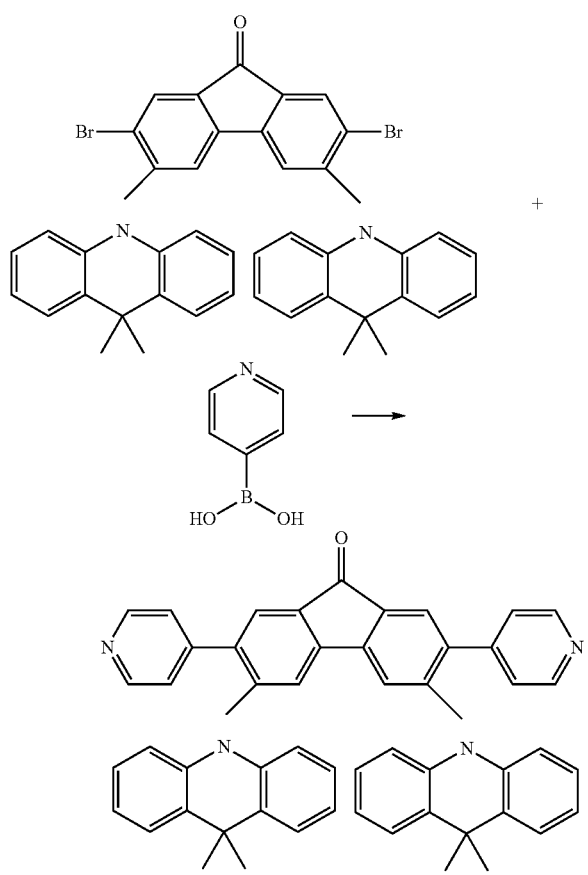

and the third reactant

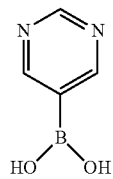

are added into a single mouth bottle, a relationship between a molar quantity of the intermediate product and a molar quantity of the third reactant is that for 5 millimoles of the first intermediate product, there are 12 millimoles of the In some embodiments, the $R_1$ group can be not as the same as the $R_2$ group. The third reactant includes a first sub-reactant and a second sub-reactant. The step of providing a third reactant, and reacting the first intermediate product and the third reactant to generate the electroluminescent material, including:

B1, providing the first sub-reactant, and reacting the first intermediate product and the first sub-reactant to generate the second intermediate product, the first sub-reactant comprises a compound containing the $R_1$ group, and a structural formula of the second intermediate product comprises

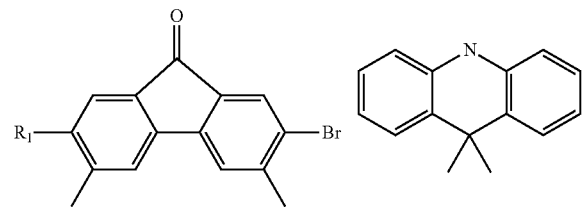

A relationship between a molar quantity of the first intermediate product and a molar quantity of the first sub-reactant is that for 5 millimoles of the first intermediate product, there are 3 millimoles-8 millimoles of the first sub-reactant.

The first intermediate product and the first sub-reactant are reacted in a third solvent to generate the second intermediate product. The third solvent includes water, N-methylpyrrolidone, toluene, ethanol, ethylene, perchloroethylene, trichloroethylene, acetone, ethylene glycol ether, triethanolamine, or combinations thereof. The third solvent includes a third additive. The third additive includes ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In one embodiment, the first intermediate product

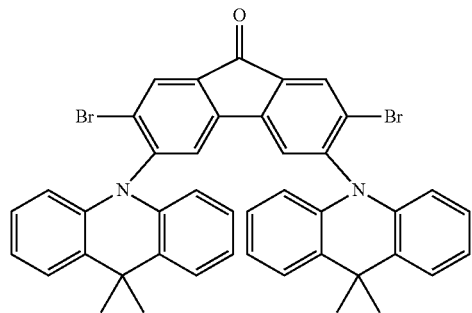 [SMILES: CC1(C)c2ccccc2N(c2cc3c(cc2Br)C(=O)c2cc(Br)c(N4c5ccccc5C(C)(C)c5ccccc54)cc2-3)c2ccccc21]

and the third reactant

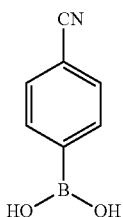

are added into a single mouth bottle, a relationship between a molar quantity of the intermediate product and a molar quantity of the first sub-reactant is that for 5 millimoles of the first intermediate product, there are 5 millimoles of the first sub-reactant, and then tetrakistriphenylphosphine palladium and anhydrous sodium carbonate are added, then toluene, ethanol and deionized water are added, those are reacted 48 hours at 100 degrees Celsius to obtain a mixture containing the second intermediate product, then a separating and purifying process is employed to obtain the second intermediate product

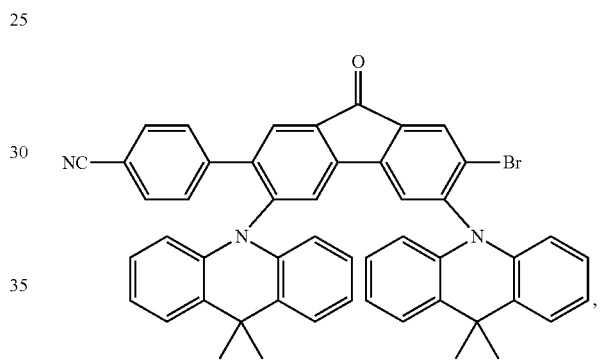

the second intermediate product is red powder.

In one embodiment of the present application, a reaction equation of the reacting the first intermediate product and the first sub-reactant is:

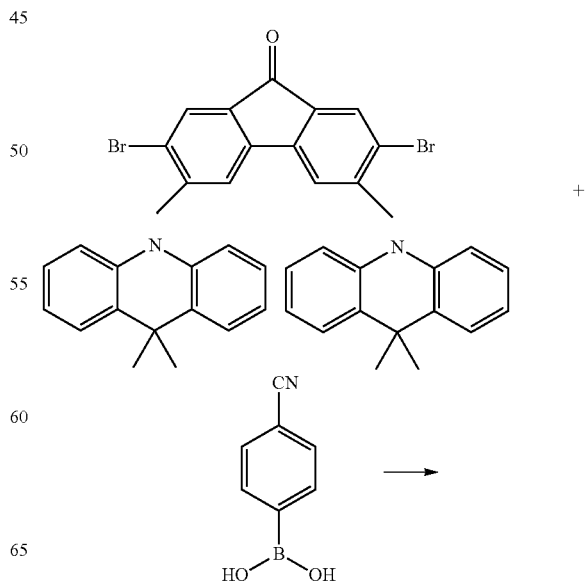

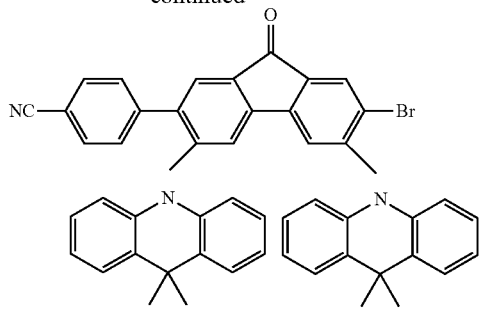

B2, providing the second sub-reactant, and reacting the second intermediate product and the second sub-reactant to generate the electroluminescent material, wherein the second reactant comprises a compound containing the $R_2$ group.

A relationship between a molar quantity of the second intermediate product and a molar quantity of the second sub-reactant is that for 4 millimoles of the second intermediate product, there are 3 millimoles-8 millimoles of the second sub-reactant.

The second intermediate product and the second sub-reactant are reacted in a fourth solvent to generate to the electroluminescent material. The fourth solvent includes water, N-methylpyrrolidone, toluene, ethanol, ethylene, perchloroethylene, trichloroethylene, acetone, ethylene glycol ether, triethanolamine, or combinations thereof. The fourth solvent includes a fourth additive. The fourth additive includes ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

In one embodiment, the second intermediate product

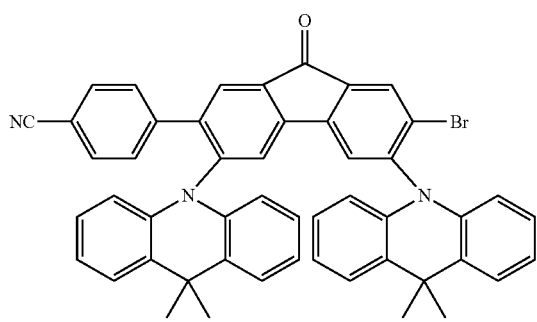 [SMILES: CC1(C)c2ccccc2N(c2cc3c(cc2Br)C(=O)c2cc(-c4ccc(C#N)cc4)c(N4c5ccccc5C(C)(C)c5ccccc54)cc2-3)c2ccccc21]

and the second sub-reactant

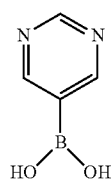

are added into a single mouth bottle, a relationship between a molar quantity of the second intermediate product and a molar quantity of the second sub-reactant is that for 4 millimoles of the second intermediate product, there are 6 millimoles of the second sub-reactant, and then tetrakistriphenylphosphine palladium and anhydrous sodium carbonate are added, then toluene, ethanol and deionized water are added, those are reacted 48 hours at 100 degrees Celsius to obtain a mixture containing the electroluminescent material, then a separating and purifying process is employed to obtain the electroluminescent material

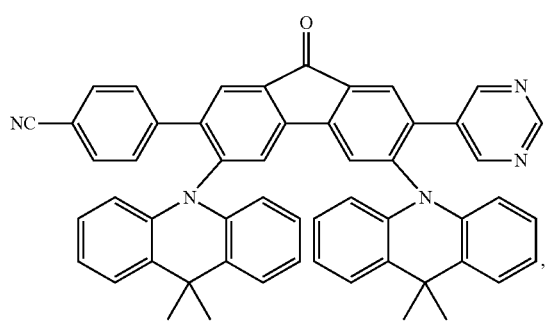 [SMILES: CC1(C)c2ccccc2N(c2cc3c(cc2-c2ccc(C#N)cc2)C(=O)c2cc(-c4cncnc4)c(N4c5ccccc5C(C)(C)c5ccccc54)cc2-3)c2ccccc21]

the electroluminescent is red powder.

In one embodiment of the present application, a reaction equation of the reacting the second intermediate product and the second sub-reactant is:

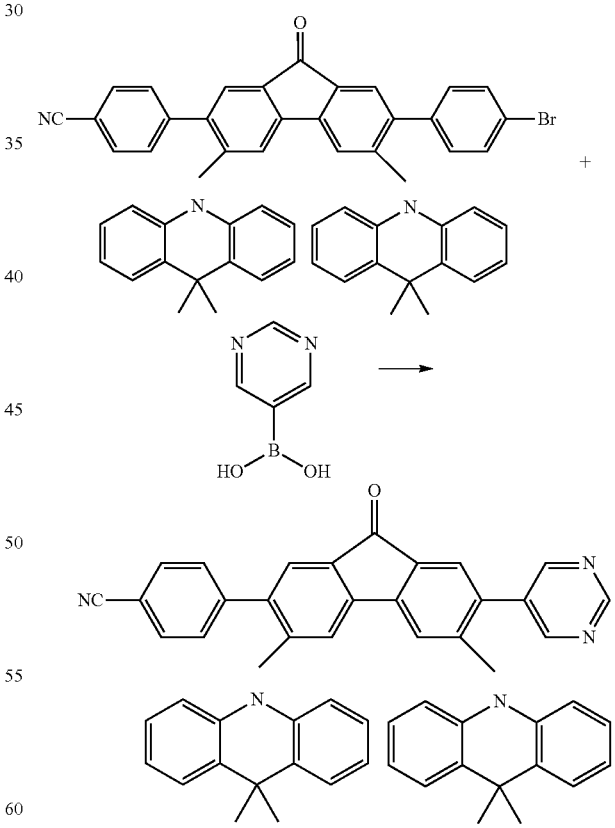

In the separating and purifying process, first, the reaction solution is cooled down to room temperature, quenched by employing saturated saline, and extracted twice to five times by an extraction solvent, organic phases are selected, spun into silica gel, and employed chromatography by a chromatographic column to obtain a red powder which is defined as the electroluminescent material. A yield of the electroluminescent material is more than or equal to 60%.

The extraction solvent includes dichloromethane, chloroform, tetrahydrofuran, or combinations thereof. In the chromatographic column, the dichloromethane and the n-hexane have a volume ration ranging from 1:0.5 to 1:10.

Referring to FIG. 1, FIG. 1 is a schematic structural view of a light emitting device of the present application.

The present application provides a light emitting device 10. The light emitting device includes a substrate layer 11, a hole transport layer 12, an auxiliary layer 13, a light emitting layer 14, an electron transport layer 15 and a second electrode layer 16.

The substrate layer 11 includes a base 111 and a first electrode layer 112 formed on the base 111. The hole transport layer 12 is formed on the substrate layer 10. The hole transport layer 12 is electrically connected to the first electrode layer 112. The auxiliary layer 13 is formed on the hole transport layer 12. The light emitting layer 14 is formed on the auxiliary layer 13. The electron transport layer 15 is formed on the light emitting layer 14. The second electrode 16 is electrically connected to the electron transport layer 15.

The substrate layer 111 can be a glass base. The first electrode layer 112 can be made of indium tin oxide. The hole transport layer 12 can be made of 4,4'-cyclohexyl bis[N,N-bis(4-methylphenyl)aniline]. The auxiliary layer 13 can be made of 4,4',4"-tris(carbazol-9-yl)triphenylamine. The electron transport layer 15 can be made of 1,3,5-tris(3-(3-pyridyl)phenyl)benzene (Tm3PyPB). The second electrode layer 15 can be made of lithium fluoride/aluminum (LiF/Al). The light emitting layer 14 includes the electroluminescent material, and a structural formula of the electroluminescent material is

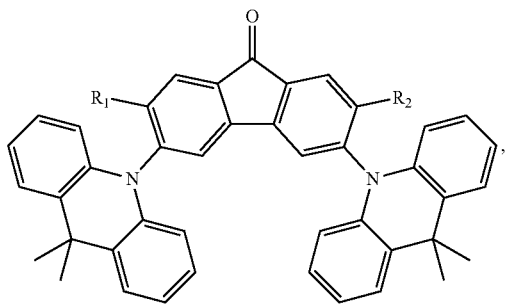

wherein a structural formula of R₁ group comprises one of

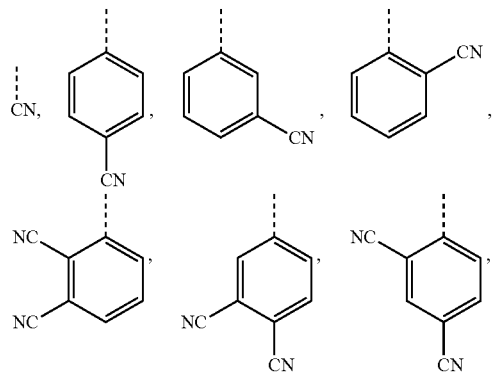

-continued

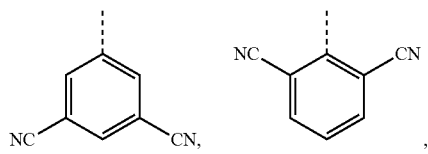

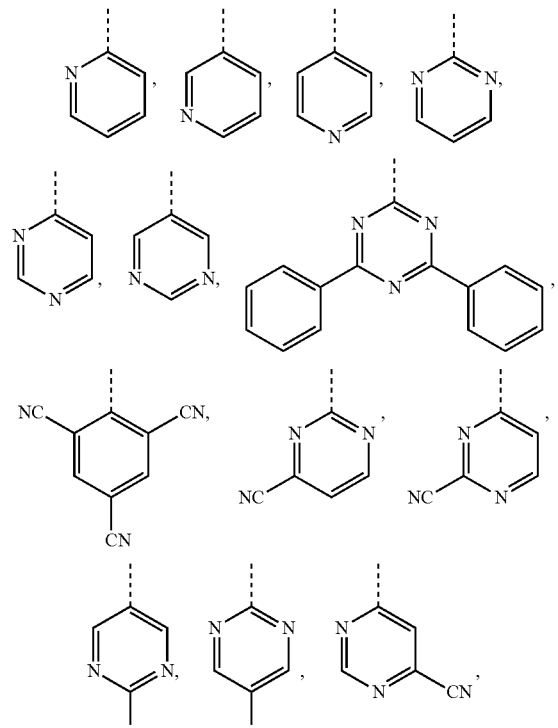

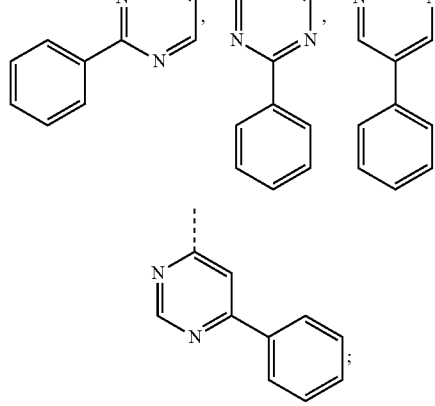

and a structural formula of R2 group comprises one of
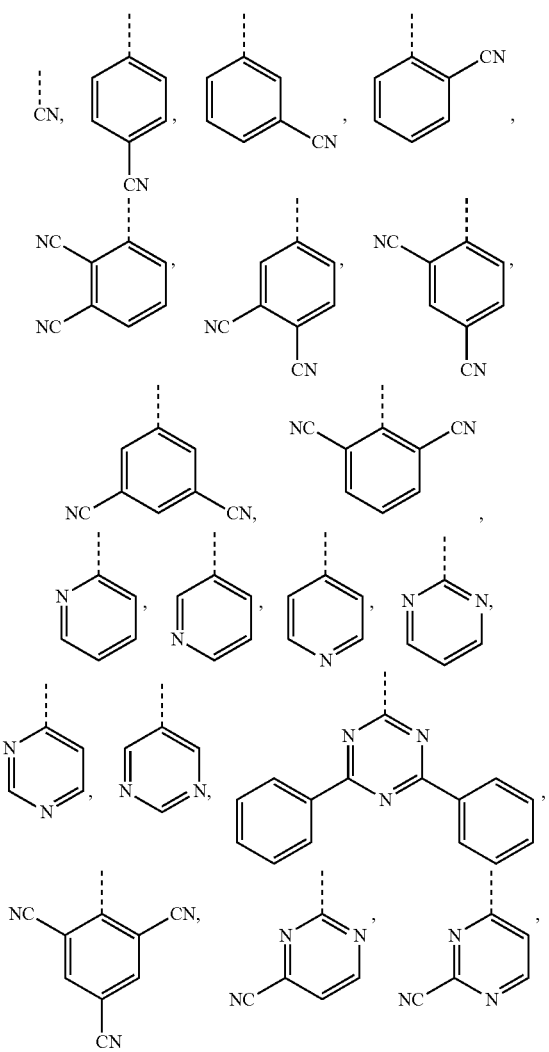
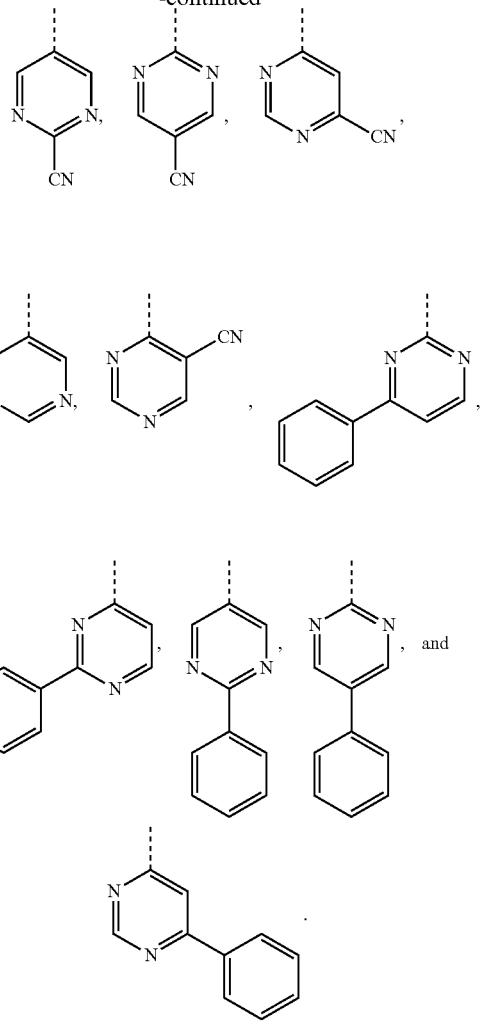
, and
Referring to table 1, table 1 is a performance data of the light emitting device of the present application.
| Light Emitting Device | Electroluminescent Material | Max Luminance (cd/m$^2$) | Max Current Efficiency (cd/A) | Color Coordinates CIEx | Max External Quantum Efficiency (%) |
|---|---|---|---|---|---|
| 1 | 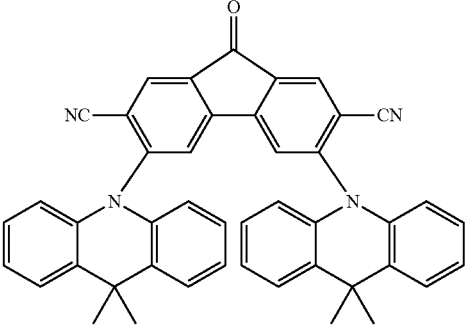 [SMILES: CC1(C)c2ccccc2N(c2cc3c(cc2C#N)C(=O)c2cc(C#N)c(N4c5ccccc5C(C)(C)c5ccccc54)cc2-3)c2ccccc21] | 2356 | 24.8 | 0.568 | 16.8 |

-continued
| Light Emitting Device | Electroluminescent Material | Max Luminance (cd/m²) | Max Current Efficiency (cd/A) | Color Coordinates CIEx | Max External Quantum Efficiency (%) |
|---|---|---|---|---|---|
| 2 | 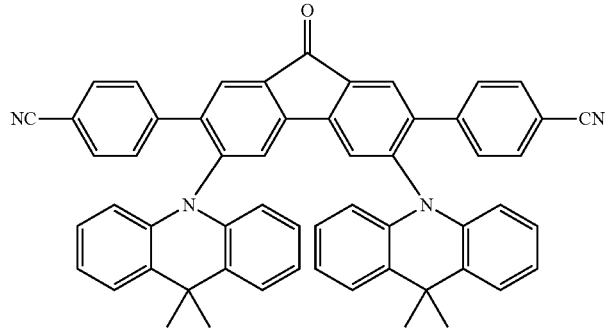 [SMILES: CC1(C)c2ccccc2N(c2cc3c(cc2-c2ccc(C#N)cc2)C(=O)c2cc(-c4ccc(C#N)cc4)c(N4c5ccccc5C(C)(C)c5ccccc54)cc2-3)c2ccccc21] | 2178 | 23.3 | 0.562 | 15.9 |
| 3 | 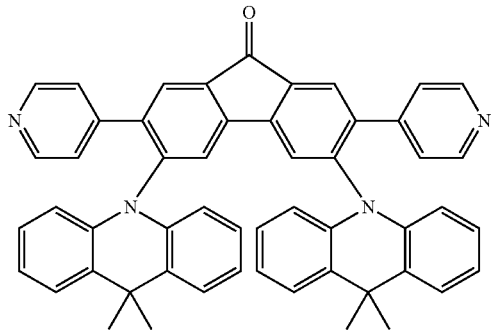 [SMILES: CC1(C)c2ccccc2N(c2cc3c(cc2-c2ccncc2)C(=O)c2cc(-c4ccncc4)c(N4c5ccccc5C(C)(C)c5ccccc54)cc2-3)c2ccccc21] | 1781 | 21.2 | 0.557 | 12.1 |
| 4 | 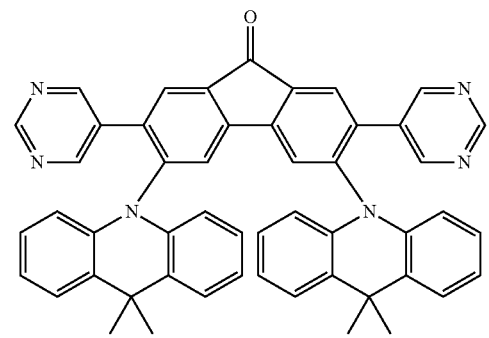 [SMILES: CC1(C)c2ccccc2N(c2cc3c(cc2-c2cncnc2)C(=O)c2cc(-c4cncnc4)c(N4c5ccccc5C(C)(C)c5ccccc54)cc2-3)c2ccccc21] | 1805 | 23.6 | 0.563 | 14.7 |
| 5 | 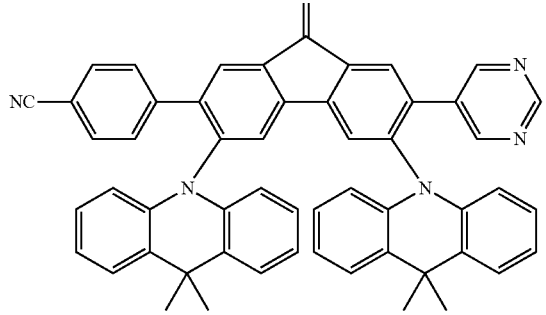 | 1874 | 19.5 | 0.560 | 10.4 |

The present application provides an electroluminescent material, a method for manufacturing the electroluminescent material, and a light emitting device, and a structural formula of the electroluminescent material is

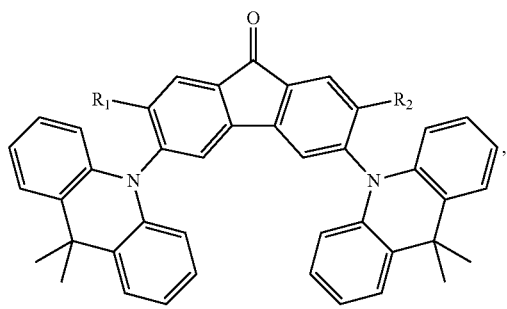

wherein structural formulas of the $R_1$ and $R_2$ are selected from

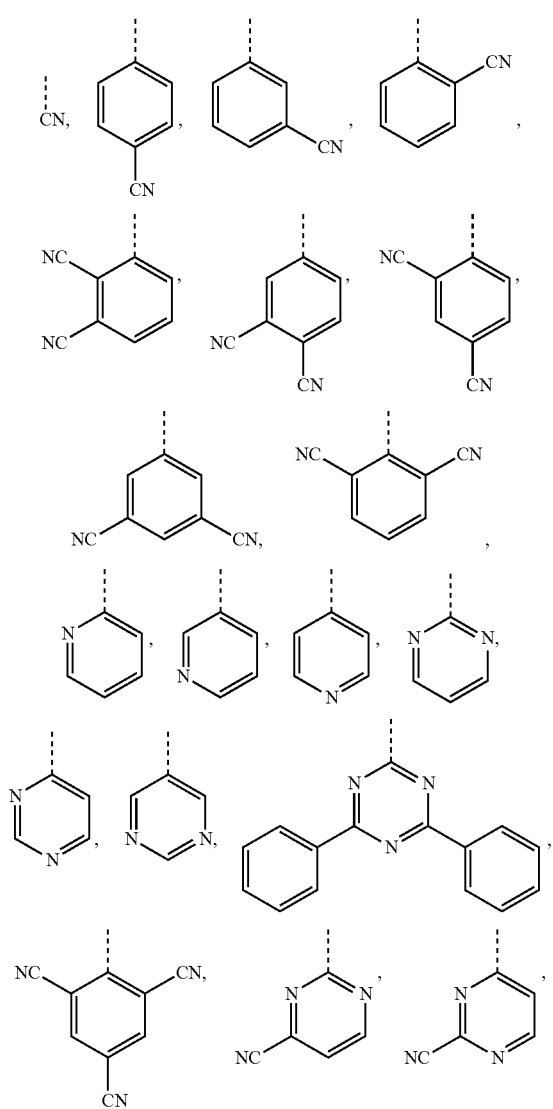

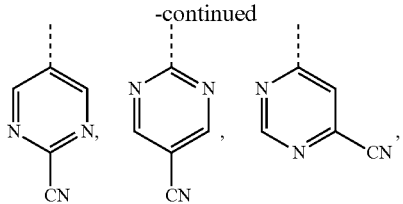

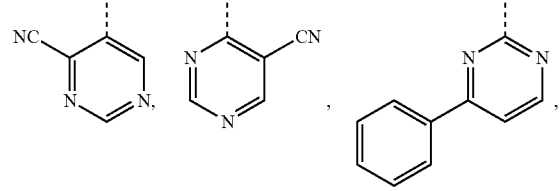

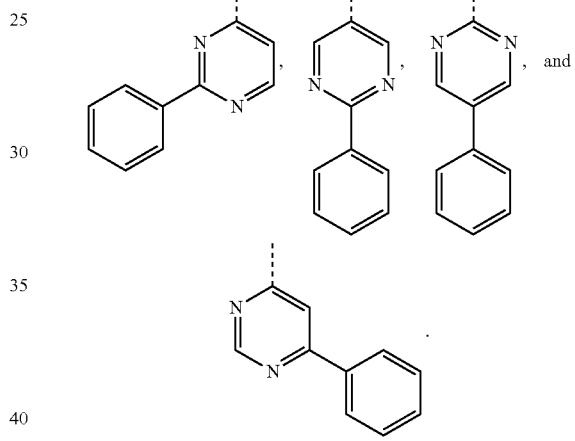

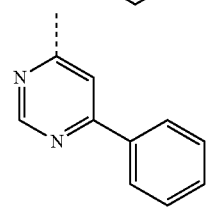

by employing the strong electron-withdrawing group such as cyano, pyridine, pyrimidine, or s-triazine to enhance the electron-withdrawing property of the fluorenone receptor unit, a captodative electron effect between the electron donor unit and the electron acceptor unit in the molecule is enhanced, so that the intermolecular charge transfer property is enhanced while the red light shifts, thereby further reducing the energy level difference between the single-line energy level and the triplet energy level of the target molecule, to realize a long life span, red light emitted electroluminescent material, a method for manufacturing the electroluminescent material and a light emitting device.

As is understood by persons skilled in the art, the foregoing preferred embodiments of the present application are illustrative rather than limiting of the present application. It is intended that they cover various modifications and that similar arrangements be included in the spirit and scope of the present application, the scope of which should be accorded the broadest interpretation so as to encompass all such modifications and similar structures.

What is claimed is:

1. An electroluminescent material, wherein a structural formula of the electroluminescent material is

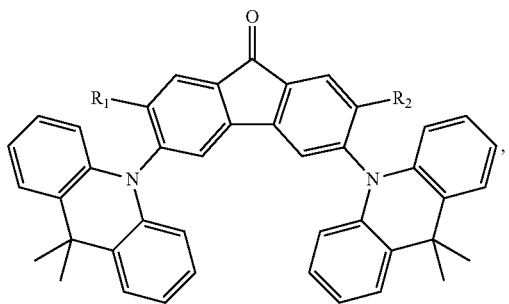
wherein a structural formula of R₁ group comprises one of
and a structural formula of R₂ group comprises one of -continued

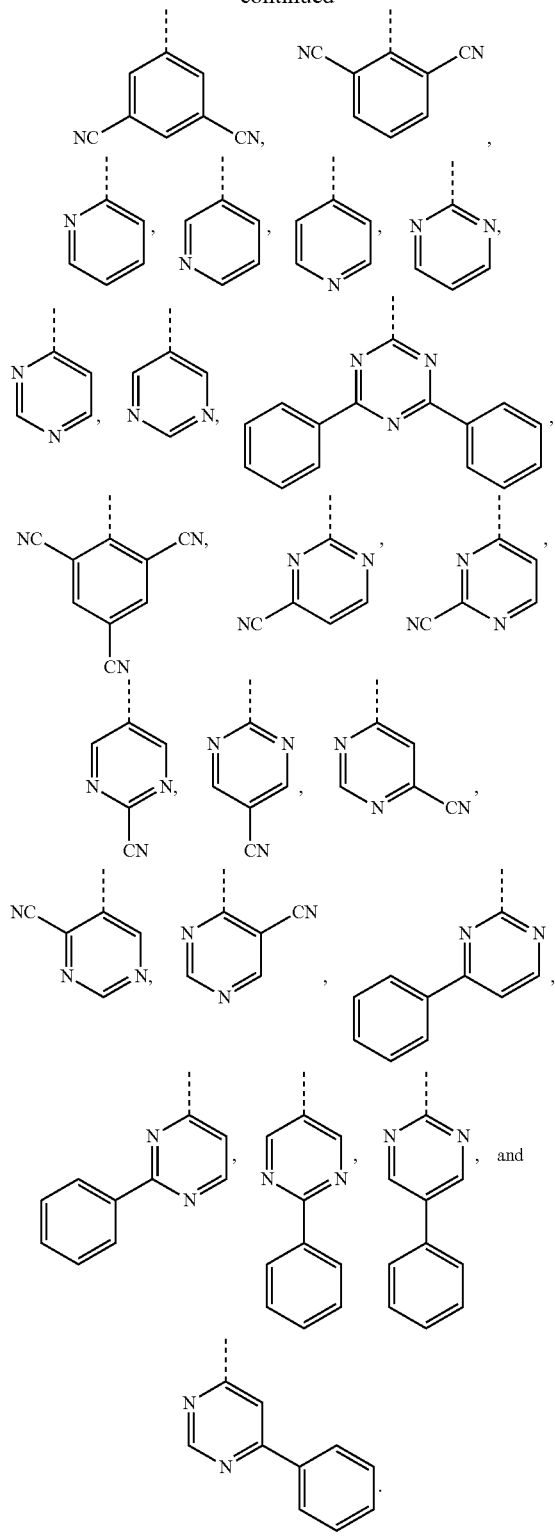

2. A method for manufacturing an electroluminescent material, comprising:
providing a first reactant and a second reactant, and reacting the first reactant and the second reactant to generate a first intermediate product, wherein a structural formula of the first reactant is

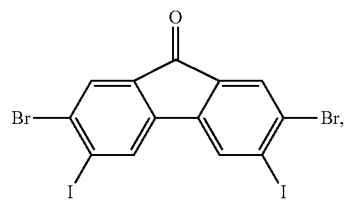 [SMILES: O=C1c2cc(Br)c(I)cc2-c2cc(I)c(Br)cc21]

a structural formula of the second reactant is

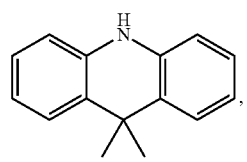 [SMILES: CC1(C)c2ccccc2Nc2ccccc21]

and a structural formula of the first intermediate product is

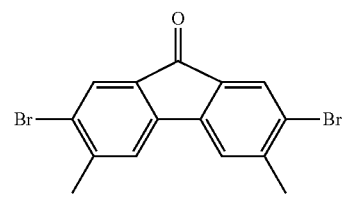

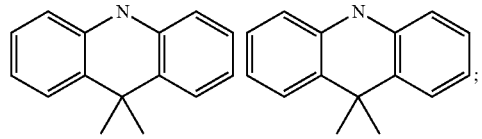

and providing a third reactant, and reacting the first intermediate product and the third reactant to generate the electroluminescent material, wherein the third reactant comprises a compound containing $R_1$ group and a compound containing $R_2$ group, and a structural formula of the electroluminescent material is

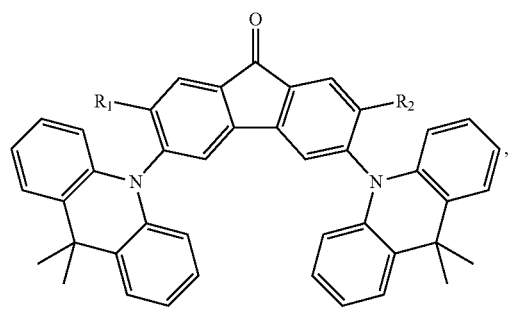

wherein a structural formula of R₁ group comprises one of
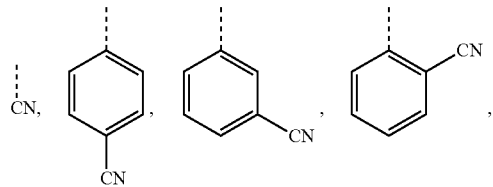
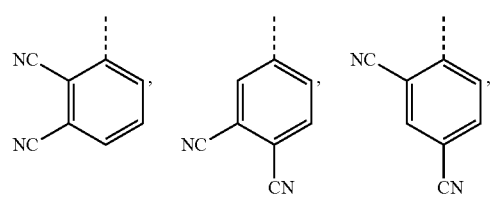
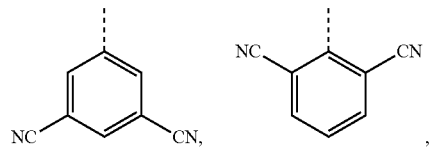
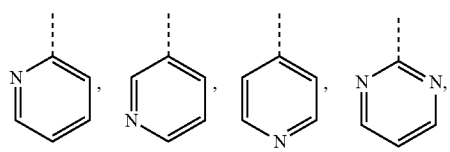
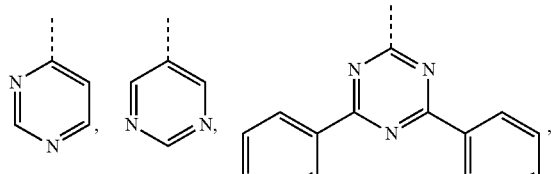
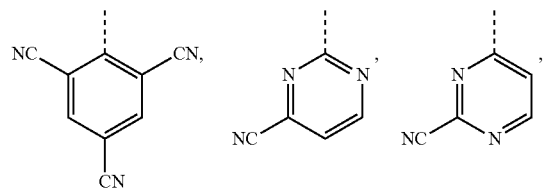
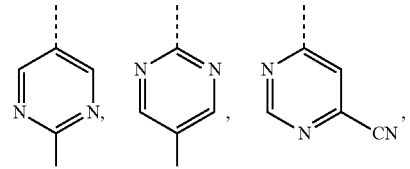
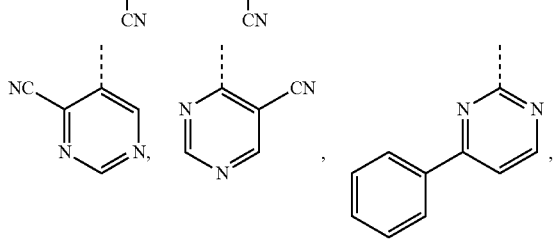
and a structural formula of R₂ group comprises one of
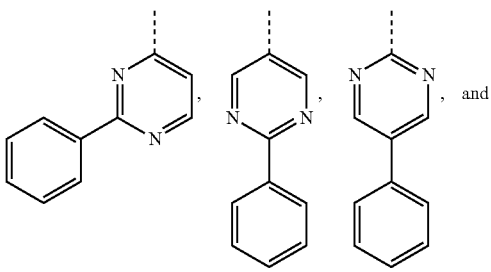
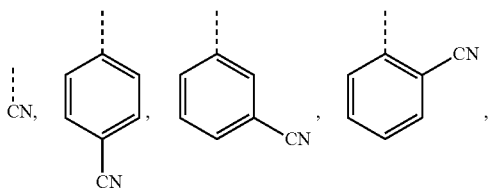
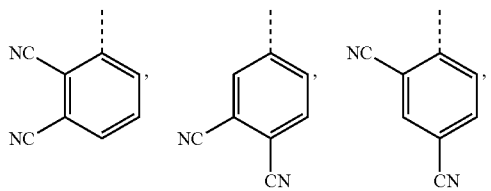
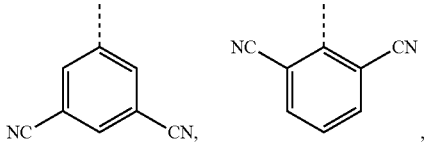
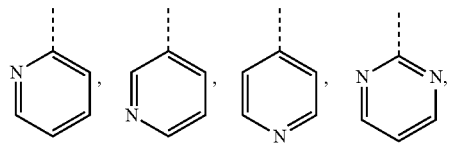
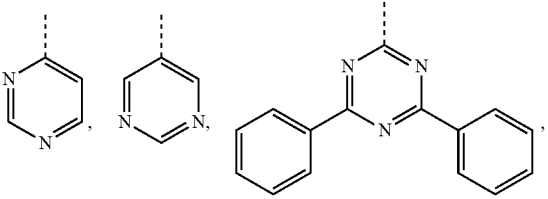
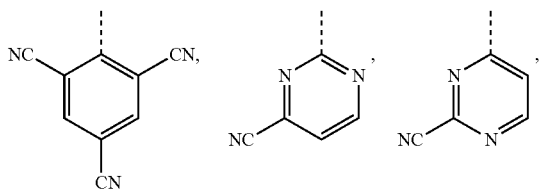

-continued

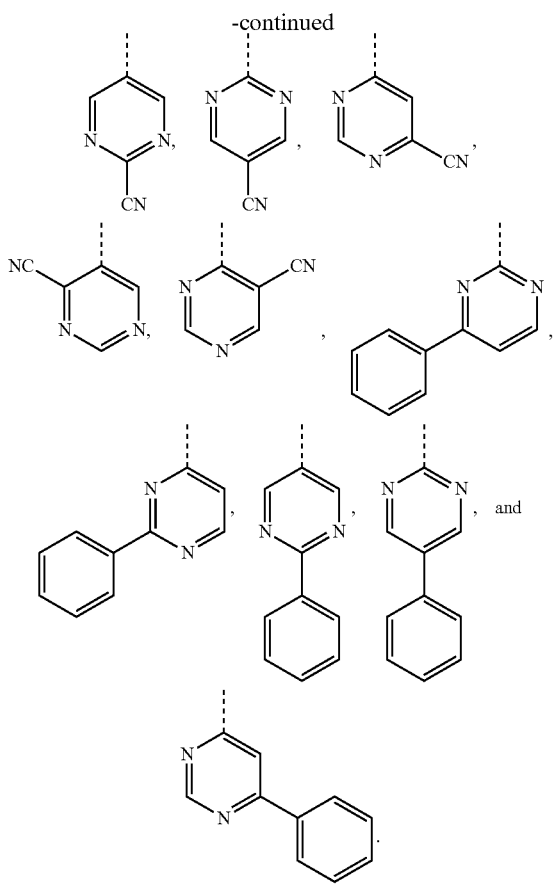

3. The method for manufacturing the electroluminescent material of claim 2, wherein in the step of reacting the first reactant and the second reactant to generate a first intermediate product, a relationship between a molar quantity of the first reactant and a molar quantity of the second reactant is that for 10 millimoles of the first reactant, there are 15 millimoles-25 millimoles of the second reactant.

4. The method for manufacturing the electroluminescent material of claim 3, wherein the first reactant and the second reactant are reacted in a first solvent to generate the first intermediate product, and the first solvent comprises toluene, ethanol, ethylene, perchloroethylene, trichloroethylene, acetone, ethylene glycol ether, triethanolamine, or combinations thereof.

5. The method for manufacturing the electroluminescent material of claim 4, wherein the first solvent comprises a first additive, and the first additive comprises tris(dibenzylideneacetone)dipalladium, tetrakistriphenylphosphine palladium, 9,10-dihydro-9,9-diphenyl acridine, bis(2-diphenylphosphinophenyl)ether, cesium carbonate, potassium hydroxide, sodium hydroxide, sodium tert-butoxide, sodium bicarbonate, or combinations thereof.

6. The method for manufacturing the electroluminescent material of claim 2, wherein in the step of providing a third reactant, and reacting the first intermediate product and the third reactant to generate the electroluminescent material, the $R_1$ group and the $R_2$ group are the same, a relationship between a molar quantity of the first intermediate product and a molar quantity of the third reactant is that for 5 millimoles of the first intermediate product, there are 10 millimoles-40 millimoles of the third reactant.

7. The method for manufacturing the electroluminescent material of claim 6, wherein the first intermediate product and the third reactant are reacted in a second solvent to generate the electroluminescent material, and the second solvent comprises water, N-methylpyrrolidone, toluene, ethanol, ethylene, perchloroethylene, trichloroethylene, acetone, ethylene glycol ether, triethanolamine, or combinations thereof.

8. The method for manufacturing the electroluminescent material of claim 7, wherein the second solvent comprises a second additive, and the second additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

9. The method for manufacturing the electroluminescent material of claim 2, wherein in the step of providing a third reactant, and reacting the first intermediate product and the third reactant to generate the electroluminescent material, the $R_1$ group and the $R_2$ group are different, and the third reactant comprises a first sub-reactant and a second sub-reactant, wherein the step of providing a third reactant, and reacting the first intermediate product and the third reactant to generate the electroluminescent material comprises:

providing the first sub-reactant, and reacting the first intermediate product and the first sub-reactant to generate the second intermediate product, the first sub-reactant comprises a compound containing the $R_1$ group, and a structural formula of the second intermediate product comprises

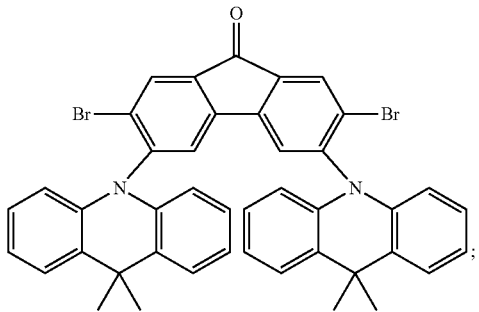 [SMILES: CC1(C)c2ccccc2N(c2cc3c(cc2Br)C(=O)c2cc(Br)c(N4c5ccccc5C(C)(C)c5ccccc54)cc2-3)c2ccccc21]

and providing the second sub-reactant, and reacting the second intermediate product and the second sub-reactant to generate the electroluminescent material, wherein the second reactant comprises a compound containing the $R_2$ group.

10. The method for manufacturing the electroluminescent material of claim 9, wherein in the step of providing a first sub-reactant, and reacting the first intermediate product and the first sub-reactant to generate the second intermediate product, a relationship between a molar quantity of the first intermediate product and a molar quantity of the first sub-reactant is that for 5 millimoles of the first intermediate product, there are 3 millimoles-8 millimoles of the first sub-reactant.

11. The method for manufacturing the electroluminescent material of claim 10, wherein the first intermediate product and the first sub-reactant are reacted in a third solvent to generate the second intermediate product, the third solvent comprises water, N-methylpyrrolidone, toluene, ethanol, ethylene, perchloroethylene, trichloroethylene, acetone, ethylene glycol ether, triethanolamine, or combinations thereof.

12. The method for manufacturing the electroluminescent material of claim 11, wherein the third solvent comprises a third additive, and the third additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

13. The method for manufacturing the electroluminescent material of claim 9, wherein in the step of providing a second sub-reactant, and reacting the second intermediate product and the second sub-reactant to generate the electroluminescent material, a relationship between a molar quantity of the second intermediate product and a molar quantity of the second sub-reactant is that for 4 millimoles of the second intermediate product, there are 3 millimoles-8 millimoles of the second sub-reactant.

14. The method for manufacturing the electroluminescent material of claim 13, wherein the second intermediate product and the second sub-reactant are reacted in a fourth solvent to generate to the electroluminescent material, the fourth solvent comprises water, N-methylpyrrolidone, toluene, ethanol, ethylene, perchloroethylene, trichloroethylene, acetone, ethylene glycol ether, triethanolamine, or combinations thereof.

15. The method for manufacturing the electroluminescent material of claim 14, wherein the fourth solvent comprises a fourth additive, the fourth additive comprises ferric chloride concentrated hydrochloric acid solution, palladium acetate, tri-tert-butylphosphine tetrafluoroborate, potassium hydroxide, tetrakistriphenylphosphine palladium, sodium hydroxide, sodium t-butoxide, sodium carbonate, sodium bicarbonate, or combinations thereof.

16. The method for manufacturing the electroluminescent material of claim 2, wherein the step of providing a third reactant, and reacting the first intermediate product and the third reactant to generate the electroluminescent material comprises:
    providing a third reactant, and reacting the first intermediate product and the third reactant to generate a mixture containing the electroluminescent material; and
    separating and purifying the mixture containing the electroluminescent material to obtain the electroluminescent material.

17. The method for manufacturing the electroluminescent material of claim 16, wherein in the step of separating and purifying the mixture containing the electroluminescent material to obtain the electroluminescent material, an extraction solvent is employed to extract the mixture, and a chromatographic column is employed for chromatography.

18. The method for manufacturing the electroluminescent material of claim 17, wherein the extraction solvent comprises dichloromethane, chloroform, tetrahydrofuran, or combinations thereof.

19. The method for manufacturing the electroluminescent material of claim 17, wherein in the chromatographic column, the dichloromethane and the n-hexane have a volume ration ranging from 1:0.5 to 1:10.

20. A light emitting device, comprising:
    a substrate layer, wherein the substrate layer comprises a base and a first electrode layer formed on the base;
    a hole transport layer, wherein the hole transport layer is formed on the substrate layer, and is electrically connected to the first electrode layer;
    an auxiliary layer, wherein the auxiliary layer is formed on the hole transport layer;
    a light emitting layer, wherein the light emitting layer is formed on the auxiliary layer;
    an electron transport layer, wherein the electron transport layer is formed on the light emitting layer; and
    a second electrode layer, wherein the second electrode is electrically connected to the electron transport layer, wherein the light emitting layer comprises the electroluminescent material, and a structural formula of the electroluminescent material is

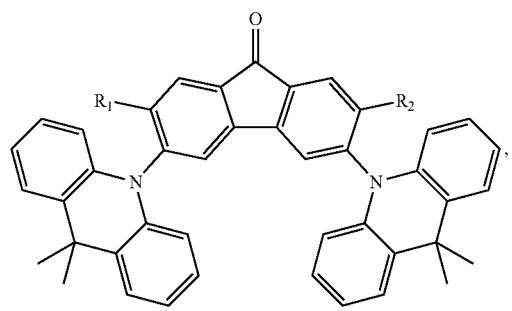

wherein a structural formula of $R_1$ group comprises one of

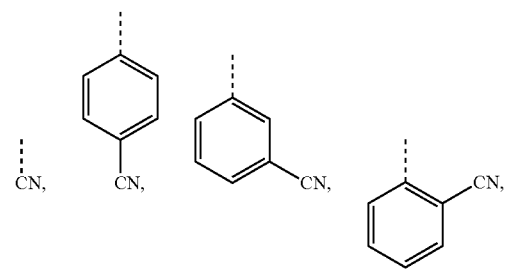

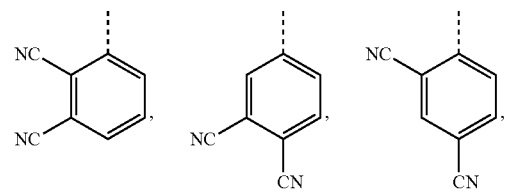

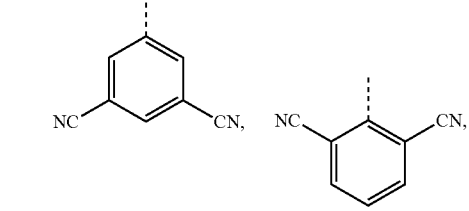

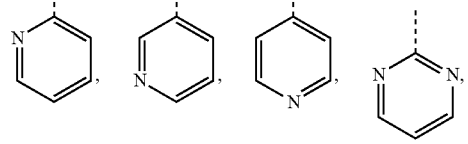

-continued
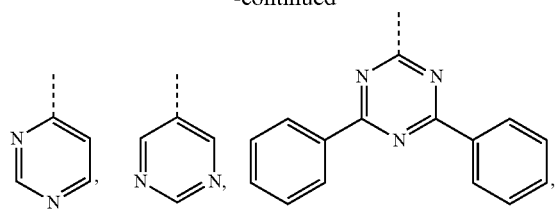
and a structural formula of R2 group comprises one of
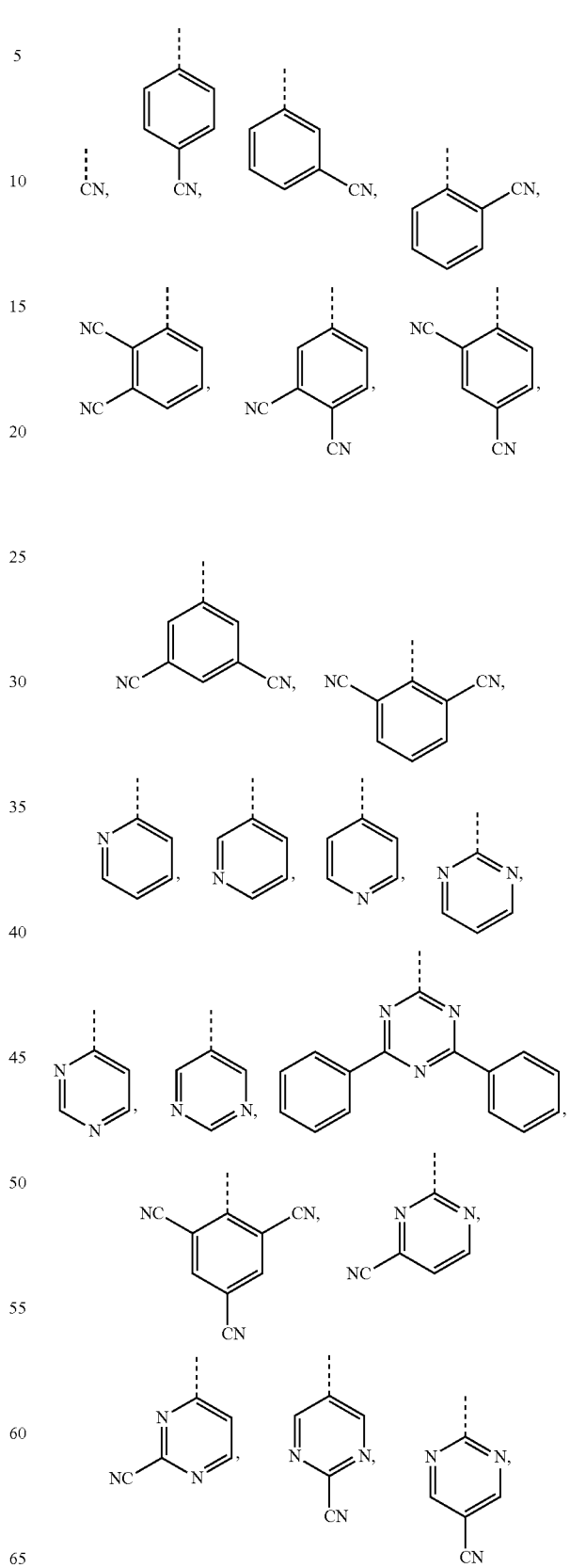

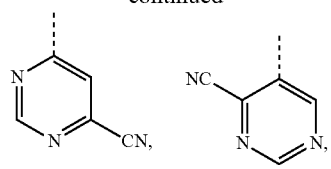
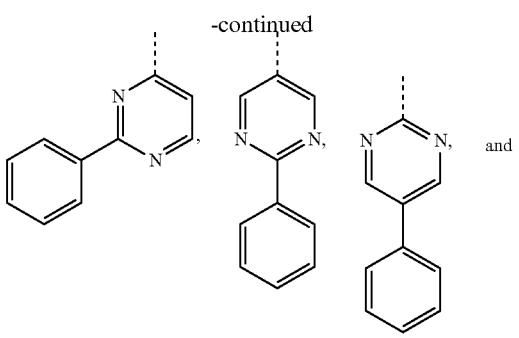
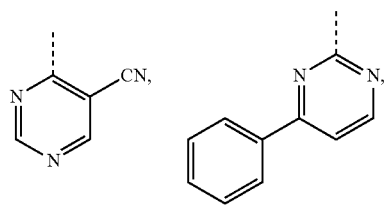
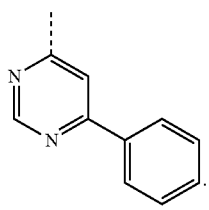
* * * * *